(12) United States Patent
Sartor et al.

(10) Patent No.: US 12,243,634 B2
(45) Date of Patent: *Mar. 4, 2025

(54) SYSTEMS AND METHODS FOR PROVIDING ASSISTANCE DURING SURGERY

(71) Applicant: Covidien LP, Mansfield, MA (US)

(72) Inventors: Joe D. Sartor, Longmont, CO (US); Francesca Rossetto, Longmont, CO (US); Irena Cantrall, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/217,891

(22) Filed: Jul. 3, 2023

(65) Prior Publication Data

US 2023/0352148 A1  Nov. 2, 2023

Related U.S. Application Data

(63) Continuation of application No. 16/046,137, filed on Jul. 26, 2018, now Pat. No. 11,705,238.

(51) Int. Cl.
*G16H 30/20* (2018.01)
*G16H 20/40* (2018.01)

(52) U.S. Cl.
CPC ............ *G16H 30/20* (2018.01); *G16H 20/40* (2018.01)

(58) Field of Classification Search
None
See application file for complete search history.

(56) References Cited

U.S. PATENT DOCUMENTS

| 5,057,494 A | 10/1991 | Sheffield |
| 5,321,113 A | 6/1994 | Cooper et al. |

(Continued)

FOREIGN PATENT DOCUMENTS

| BR | 0013237 A | 7/2003 |
| BR | 0116004 A | 6/2004 |

(Continued)

OTHER PUBLICATIONS

Australian Examination Report dated May 25, 2018 in AU Appln. No. 2017202106.

(Continued)

*Primary Examiner* — Peter H Choi
*Assistant Examiner* — John P Go
(74) *Attorney, Agent, or Firm* — Weber Rosselli & Cannon LLP

(57) ABSTRACT

A method of performing a surgical procedure includes storing a software application on a memory associated with a computer, which when executed by a processor causes the software application to develop a model of a patient's anatomical structure, process images of the patient's anatomy, display the images of the patient's anatomy on a user interface associated with the computer, superimpose critical structures within the patient over the displayed images of the patient's anatomy, determine a location within the patient's body cavity where the images of the patient's anatomy were taken, and display the model of the patient's anatomical structure on the user interface, the displayed model indicating the determined location where the images of the patient's anatomy were taken.

20 Claims, 13 Drawing Sheets

(56) References Cited

U.S. PATENT DOCUMENTS

| | | | |
|---|---|---|---|
| 6,003,517 A | 12/1999 | Sheffield et al. | |
| 6,188,355 B1 | 2/2001 | Gilboa | |
| 6,503,195 B1 | 1/2003 | Keller et al. | |
| 6,833,814 B2 | 12/2004 | Gilboa et al. | |
| 8,335,359 B2 | 12/2012 | Fidrich et al. | |
| 8,706,184 B2 | 4/2014 | Mohr et al. | |
| 8,827,934 B2 | 9/2014 | Chopra et al. | |
| 8,828,023 B2 | 9/2014 | Neff et al. | |
| 9,247,992 B2 | 2/2016 | Ladtkow et al. | |
| 9,259,269 B2 | 2/2016 | Ladtkow et al. | |
| 9,375,268 B2 | 6/2016 | Long | |
| 9,459,770 B2 | 10/2016 | Baker | |
| 9,538,962 B1* | 1/2017 | Hannaford | G16H 40/63 |
| 9,575,140 B2 | 2/2017 | Zur | |
| 9,770,216 B2 | 9/2017 | Brown et al. | |
| 9,918,659 B2 | 3/2018 | Chopra et al. | |
| 10,004,558 B2 | 6/2018 | Long et al. | |
| 10,194,897 B2 | 2/2019 | Cedro et al. | |
| 10,373,719 B2 | 8/2019 | Soper et al. | |
| 10,376,178 B2 | 8/2019 | Chopra | |
| 10,405,753 B2 | 9/2019 | Sorger | |
| 10,478,162 B2 | 11/2019 | Barbagli et al. | |
| 10,480,926 B2 | 11/2019 | Froggatt et al. | |
| 10,524,866 B2 | 1/2020 | Srinivasan et al. | |
| 10,555,788 B2 | 2/2020 | Panescu et al. | |
| 10,569,071 B2 | 2/2020 | Harris et al. | |
| 10,603,106 B2 | 3/2020 | Weide et al. | |
| 10,610,306 B2 | 4/2020 | Chopra | |
| 10,638,953 B2 | 5/2020 | Duindam et al. | |
| 10,639,114 B2 | 5/2020 | Schuh et al. | |
| 10,674,970 B2 | 6/2020 | Averbuch et al. | |
| 10,682,070 B2 | 6/2020 | Duindam | |
| 10,702,137 B2 | 7/2020 | Deyanov | |
| 10,706,543 B2 | 7/2020 | Donhowe et al. | |
| 10,709,506 B2 | 7/2020 | Coste-Maniere et al. | |
| 10,772,485 B2 | 9/2020 | Schlesinger et al. | |
| 10,796,432 B2 | 10/2020 | Mintz et al. | |
| 10,823,627 B2 | 11/2020 | Sanborn et al. | |
| 10,827,913 B2 | 11/2020 | Ummalaneni et al. | |
| 10,835,153 B2 | 11/2020 | Rafii-Tari et al. | |
| 10,885,630 B2 | 1/2021 | Li et al. | |
| 2002/0147462 A1 | 10/2002 | Mair et al. | |
| 2003/0013972 A1 | 1/2003 | Makin | |
| 2003/0095692 A1 | 5/2003 | Mundy et al. | |
| 2003/0164952 A1 | 9/2003 | Deichmann et al. | |
| 2004/0120981 A1 | 6/2004 | Nathan | |
| 2006/0189842 A1* | 8/2006 | Hoeg | A61B 90/36 600/109 |
| 2006/0253030 A1 | 11/2006 | Altmann et al. | |
| 2008/0045938 A1 | 2/2008 | Weide et al. | |
| 2008/0172383 A1 | 7/2008 | Lea et al. | |
| 2008/0243142 A1 | 10/2008 | Gildenberg | |
| 2009/0284255 A1 | 11/2009 | Zur | |
| 2010/0312096 A1 | 12/2010 | Guttman et al. | |
| 2011/0085720 A1 | 4/2011 | Averbuch | |
| 2011/0236868 A1* | 9/2011 | Bronstein | G09B 23/30 434/267 |
| 2012/0120091 A1 | 5/2012 | Koudijs et al. | |
| 2012/0184844 A1 | 7/2012 | Gielen et al. | |
| 2012/0188352 A1 | 7/2012 | Wittenberg et al. | |
| 2012/0190923 A1 | 7/2012 | Kunz et al. | |
| 2012/0327186 A1* | 12/2012 | Kitamura | A61B 1/00045 348/45 |
| 2013/0063434 A1 | 3/2013 | Miga et al. | |
| 2013/0303945 A1 | 11/2013 | Blumenkranz et al. | |
| 2014/0022283 A1 | 1/2014 | Chan et al. | |
| 2014/0035798 A1 | 2/2014 | Kawada et al. | |
| 2014/0336461 A1 | 11/2014 | Reiter et al. | |
| 2015/0046818 A1 | 2/2015 | Wade et al. | |
| 2015/0148690 A1 | 5/2015 | Chopra et al. | |
| 2015/0265257 A1 | 9/2015 | Costello et al. | |
| 2015/0265368 A1 | 9/2015 | Chopra et al. | |
| 2016/0000302 A1 | 1/2016 | Brown et al. | |
| 2016/0000356 A1 | 1/2016 | Brown et al. | |
| 2016/0005193 A1 | 1/2016 | Markov et al. | |
| 2016/0038248 A1 | 2/2016 | Bharadwaj et al. | |
| 2016/0073854 A1 | 3/2016 | Zeien | |
| 2016/0157939 A1 | 6/2016 | Larkin et al. | |
| 2016/0183841 A1 | 6/2016 | Duindam et al. | |
| 2016/0192860 A1 | 7/2016 | Allenby et al. | |
| 2016/0287344 A1 | 10/2016 | Donhowe et al. | |
| 2017/0112571 A1 | 4/2017 | Thiel et al. | |
| 2017/0112576 A1 | 4/2017 | Coste-Maniere et al. | |
| 2017/0135760 A1 | 5/2017 | Girotto et al. | |
| 2017/0209071 A1 | 7/2017 | Zhao et al. | |
| 2017/0258526 A1 | 9/2017 | Lang | |
| 2017/0265952 A1 | 9/2017 | Donhowe et al. | |
| 2017/0280970 A1 | 10/2017 | Sartor et al. | |
| 2017/0311844 A1 | 11/2017 | Zhao et al. | |
| 2017/0319165 A1 | 11/2017 | Averbuch | |
| 2017/0345155 A1 | 11/2017 | Higgins et al. | |
| 2017/0361093 A1 | 12/2017 | Yoo et al. | |
| 2018/0078318 A1 | 3/2018 | Barbagli et al. | |
| 2018/0085079 A1 | 3/2018 | Krimsky | |
| 2018/0144092 A1 | 5/2018 | Flitsch et al. | |
| 2018/0146839 A1 | 5/2018 | Friedlander et al. | |
| 2018/0153621 A1 | 6/2018 | Duindam et al. | |
| 2018/0161102 A1 | 6/2018 | Wei et al. | |
| 2018/0235709 A1 | 8/2018 | Donhowe et al. | |
| 2018/0240237 A1 | 8/2018 | Donhowe et al. | |
| 2018/0256262 A1 | 9/2018 | Duindam et al. | |
| 2018/0263706 A1 | 9/2018 | Averbuch | |
| 2018/0279852 A1 | 10/2018 | Rafii-Tari et al. | |
| 2018/0325419 A1 | 11/2018 | Zhao et al. | |
| 2019/0000559 A1 | 1/2019 | Berman et al. | |
| 2019/0000560 A1 | 1/2019 | Berman et al. | |
| 2019/0008413 A1 | 1/2019 | Duindam et al. | |
| 2019/0027252 A1 | 1/2019 | Calhoun et al. | |
| 2019/0038365 A1 | 2/2019 | Soper et al. | |
| 2019/0065209 A1 | 2/2019 | Mishra et al. | |
| 2019/0110839 A1 | 4/2019 | Rafii-Tari et al. | |
| 2019/0139216 A1 | 5/2019 | Georgescu et al. | |
| 2019/0175062 A1 | 6/2019 | Rafii-Tari et al. | |
| 2019/0175799 A1 | 6/2019 | Hsu et al. | |
| 2019/0183318 A1 | 6/2019 | Froggatt et al. | |
| 2019/0183585 A1 | 6/2019 | Rafii-Tari et al. | |
| 2019/0183587 A1 | 6/2019 | Rafii-Tari et al. | |
| 2019/0192234 A1 | 6/2019 | Gadda et al. | |
| 2019/0209016 A1 | 7/2019 | Herzlinger et al. | |
| 2019/0209043 A1 | 7/2019 | Zhao et al. | |
| 2019/0216548 A1 | 7/2019 | Ummalaneni | |
| 2019/0239723 A1 | 8/2019 | Duindam et al. | |
| 2019/0239831 A1 | 8/2019 | Chopra | |
| 2019/0250050 A1 | 8/2019 | Sanborn et al. | |
| 2019/0254649 A1 | 8/2019 | Walters et al. | |
| 2019/0269470 A1 | 9/2019 | Barbagli et al. | |
| 2019/0269818 A1 | 9/2019 | Dhanaraj et al. | |
| 2019/0269819 A1 | 9/2019 | Dhanaraj et al. | |
| 2019/0272634 A1 | 9/2019 | Li et al. | |
| 2019/0298160 A1 | 10/2019 | Ummalaneni et al. | |
| 2019/0298451 A1 | 10/2019 | Wong et al. | |
| 2019/0320878 A1 | 10/2019 | Duindam et al. | |
| 2019/0320937 A1 | 10/2019 | Duindam et al. | |
| 2019/0336238 A1 | 11/2019 | Yu et al. | |
| 2019/0343424 A1 | 11/2019 | Blumenkranz et al. | |
| 2019/0350659 A1 | 11/2019 | Wang et al. | |
| 2019/0365199 A1 | 12/2019 | Zhao et al. | |
| 2019/0365479 A1 | 12/2019 | Rafii-Tari | |
| 2019/0365486 A1 | 12/2019 | Srinivasan et al. | |
| 2019/0380787 A1 | 12/2019 | Ye et al. | |
| 2020/0000319 A1 | 1/2020 | Saadat et al. | |
| 2020/0000526 A1 | 1/2020 | Zhao | |
| 2020/0008655 A1 | 1/2020 | Schlesinger et al. | |
| 2020/0015925 A1 | 1/2020 | Scheib | |
| 2020/0030044 A1 | 1/2020 | Wang et al. | |
| 2020/0030461 A1 | 1/2020 | Sorger | |
| 2020/0038750 A1 | 2/2020 | Kojima | |
| 2020/0043207 A1 | 2/2020 | Lo et al. | |
| 2020/0046431 A1 | 2/2020 | Soper et al. | |
| 2020/0046436 A1 | 2/2020 | Tzeisler et al. | |
| 2020/0054399 A1 | 2/2020 | Duindam et al. | |
| 2020/0054408 A1 | 2/2020 | Schuh et al. | |
| 2020/0060771 A1 | 2/2020 | Lo et al. | |
| 2020/0069192 A1 | 3/2020 | Sanborn et al. | |

(56) References Cited

U.S. PATENT DOCUMENTS

| | | |
|---|---|---|
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |
| 2021/0153943 A1 | 5/2021 | Piron et al. |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 A | 12/2008 |
| CZ | 486540 B1 | 9/2016 |
| CZ | 2709512 B6 | 8/2017 |
| CZ | 2884879 B1 | 1/2020 |
| DE | 102009043523 A1 | 4/2011 |
| EP | 1644519 B1 | 12/2008 |
| EP | 2141497 A1 | 1/2010 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| JP | 11000309 | 1/1999 |
| JP | H11309 A | 1/1999 |
| JP | 2003290131 A | 10/2003 |
| JP | 2005287900 A | 10/2005 |
| JP | 2006204635 A | 8/2006 |
| JP | 2009078133 A | 4/2009 |
| JP | 2010279695 A | 12/2010 |
| JP | 2013506861 A | 2/2013 |
| MX | PA03005028 A | 1/2004 |
| MX | PA03000137 A | 9/2004 |
| MX | PA03006874 A | 9/2004 |
| MX | 225663 B | 1/2005 |
| MX | 226292 B | 2/2005 |
| MX | PA03010507 A | 7/2005 |
| MX | PA05011725 A | 5/2006 |
| MX | 06011286 | 3/2007 |
| MX | PA06011286 A | 3/2007 |
| MX | 246862 B | 6/2007 |
| MX | 2007006441 A | 8/2007 |
| MX | 265247 B | 3/2009 |
| MX | 284569 B | 3/2011 |
| WO | 0010456 A1 | 3/2000 |
| WO | 2000010456 A1 | 3/2000 |
| WO | 0167035 A1 | 9/2001 |
| WO | 2001067035 A1 | 9/2001 |
| WO | 2015149040 A1 | 10/2015 |
| WO | 2016178690 A1 | 11/2016 |

OTHER PUBLICATIONS

Canadian Office Action dated Jun. 7, 2018 issued in corresponding CA Appln. No. 2,962,695.

Chinese Office Action dated Jul. 4, 2018 issued in corresponding CN Appln. No. 201710204462.9.

European Search Report dated Aug. 3, 2017 issued in corresponding EP Application No. 17164275.4-1666.

Extended European Search Report issued in European Patent Application No. 19839962.8 dated Mar. 17, 2022.

Japanese Office Action dated Mar. 5, 2018 issued in corresponding JP Appln. No. 2017-068088.

PCT Search Report and Written Opinion issued in PCT Application No. PCT/US2019/040233 dated Oct. 15, 2019, 8 pages.

PR Web Online Visibility from Vocus, Press Release dated Apr. 10, 2018, "Aether to Launch AI Organ Printing Software," available at http://www.prweb.com/releases/2018/04/prweb15401486.htm [retrieved on Oct. 23, 2018].

Ueda, Kazuhiro, "Quantitative computer tomography for the prediction of pulmonary function after lung cancer survey: a simple method using simulation software," European Journal of Cardiothoracic Surgery 35 (2009) 414-418 (Year: 2009).

* cited by examiner

SYSTEMS AND METHODS FOR PROVIDING ASSISTANCE DURING SURGERY

CROSS-REFERENCE TO RELATED APPLICATION

This application is a continuation of U.S. patent application Ser. No. 16/046,137, filed on Jul. 26, 2018, the entire content of which is incorporated by reference herein.

BACKGROUND

Technical Field

The present disclosure relates to surgical systems, and more particularly, to systems and methods for providing assistance to a clinician performing surgery.

Description of Related Art

As technology has advanced, surgeons have begun to replace classical open surgical techniques with minimally invasive techniques such as laparoscopic and thoracoscopic surgery in an effort to minimize trauma to surrounding tissue, reduce pain, reduce scarring, and reduce the length of time the patient it required to stay in the hospital. Minimally invasive surgery, such as the thoracoscopic approach pioneered in the mid-19th century, involves the use of small incisions (from one to several), typically no larger than 3-10 mm. Originally performed using a cystoscope, advances in medical technology lead to the development of specialized instruments for use in the thoracic cavity, such as a thoracoscope, to view the anatomy within the thoracic cavity while performing the surgical procedure. In the late 20th century, Video Assisted Thoracic Surgery (VATS) was developed utilizing a fiber-optic endoscope to further reduce the size of incisions required to perform the incision and to provide clearer, more defined images of the thoracic cavity.

Concurrently, advances in medical imaging have enabled clinicians to more accurately depict the anatomy of a patient, and therefore, more accurately identify diseases and the location of any diseased tissue. These advances have enabled clinicians to more efficiently utilize minimally invasive surgical techniques, such as the thoracoscopic approach described above. Using medical imaging, such as CT (including X-ray CT, computerized axial tomography (CAT) scan, positron emission tomography (PET), and single-photon emission CT (SPECT)), a clinician is able to accurately identify lesions or other medical conditions without the need for invasive surgeries (such as an open approach or thoracotomy). Further, three-dimensional reconstructions of anatomical structures (e.g., organs, bones, tissue) are developed using the images obtained using one of the above-noted imaging modalities. Using the three-dimensional model, a clinician is able to segment various tissues from one another and assess an accurate location of the lesion within the thoracic cavity, or in one particular example, within the lungs. This segmentation further enables a clinician to determine the precise tissue segment with its affiliated vessel and bronchial branches and determine the ideal incision level for VATS procedures (such as a segmentectomy, lobectomy, pneumonectomy, or the like). The three-dimensional model and precise identification of the lesion within the lung and its associated vessel and bronchial branches enables clinicians to identify an ideal location for port placement and to develop a pathway to the location of the lesion, along which surgical instruments may be guided during the thoracoscopic procedure. Typically, a fiducial or other marker (e.g., coils or wires) is implanted proximate or near the affected tissue using fluoroscopy or other imaging modalities. Thereafter, the location of the fiducial relative to the lesion is checked using imaging and the VATS procedure is performed. However, it is possible for the fiducial to migrate within the tissue, leading to inaccurate identification of the location of the lesion during the VATS procedure, thereby leading to sub-optimal results.

In order to alleviate this issue, image-guided VATS (iVATS) was developed, which incorporates intraoperative imaging (such as fluoroscopy) to help guide the surgical tools to the identified lesion. In this manner, a clinician preoperatively plans the trajectory for the surgical tools (fiducials, forceps, staplers, biopsy device, or the like) and monitors their location within the thoracic cavity using intraoperative imaging.

As can be appreciated, the proliferation of advanced medical imaging, such as those described above, and the aforementioned video assisted surgical procedures, has created a need to store vast amounts of electronic data. Further advances in information technology and computer based applications have enabled healthcare providers to more efficiently manage patient data, such as through the implementation of health informatics. As defined by the National Library of Medicine, health informatics is "the interdisciplinary study of the design, development, adoption and application of IT-based innovations in healthcare services delivery, management and planning," and deals with the resources, devices, and methods required to optimize the acquisition, storage, retrieval, and use of information in the hospital setting. One such implementation of healthcare informatics is the hospital information system (HIS), which is comprised of several subsystems devoted to particular departments, such as radiology, laboratory, electronic medical records, and the like. The HIS facilitates communication between each subsystem and is accessible by clinicians via the intraweb or VPN.

Although the HIS is available for clinicians to use during pre-operative planning and post-operative analytics, patient data is often spread out amongst the picture archiving and communications system (PACS), the radiology information system (RIS), the electronic medical records system (EMR), laboratory information system (LIS), and the like. As can be appreciated, accessing each system individually can be time consuming and encumber the goal of health informatics, which is to provide higher quality and more efficient healthcare.

SUMMARY

The present disclosure is directed to a method of performing a surgical procedure. The method includes storing a software application on a memory associated with a computer, which when executed by a processor causes the software application to develop a model of a patient's anatomical structure, process images of the patient's anatomy, display the images of the patient's anatomy on a user interface associated with the computer, superimpose critical structures within the patient over the displayed images of the patient's anatomy, determine the location within the patient's body cavity where the images of the patient's anatomy were taken, and display the model of the patient's anatomical structure on the user interface, the displayed model indicating the determined location where the images of the patient's anatomy were taken.

In aspects, when executed by the processor, the software application may display the distance between the surgical instrument and critical structures within the patient's body cavity on the user interface.

In other aspects, when executed by the processor, the software application may display a status of pre-determined surgical steps on the user interface.

In certain aspects, when executed by the processor, the software application may display the patient's vitals on the user interface. In aspects, when executed by the processor, the software application may display a CT image associated with the location where the images of the patient's anatomy were taken.

In other aspects, when executed by the processor, the software application may display a timer associated with the duration of the surgical procedure. In certain aspects, when executed by the processor, the software application may enable a clinician to select data to display relating to the surgical procedure on the user interface.

In other aspects, the model of the patient's anatomical structure may be a model of the patient's lungs.

In aspects, when executed by the processor, the software application may identify the location of lymph nodes within the patient's lung and generates a lymph node map based on the identified locations of the lymph nodes.

In certain aspects, when executed by the processor, the software application identifies enlarged lymph nodes using patient data.

In other aspects, when executed by the processor, the software application may display the status of each lymph node on the user interface. The status relating to the position of each lymph node and which lymph nodes have been removed by the clinician.

In aspects, the model of the patient's anatomical structure may be an anatomical structure selected from the group consisting of the liver, the spleen, the kidney, and the adrenal gland.

According to another aspect the of present disclosure, a method of performing a surgical procedure includes storing a software application on a memory associated with a computer, which when executed by a processor causes the software application to develop a collapsed model of a patient's anatomical structure, display images of the patient's anatomy, display the images of the patient's anatomy on a user interface associated with the computer, superimpose critical structures within the patient over the displayed images of the patient's anatomy, determine a location within the patient's body cavity where the images of the patient's anatomy were taken, and display the collapsed model of the patient's anatomical structure on the user interface, the display model indicating the determined location where the images of the patient were taken.

In aspects, when executed by the processor, the software application may display the distance between the surgical instrument and critical structures within the patient's body cavity on the user interface.

In other aspects, when executed by the processor, the software application may display a status of pre-determined surgical steps on the user interface. In certain aspects, when executed by the processor, the software application may display the patient's vitals on the user interface.

In aspects, when executed by the processor, the software application may display a CT image associated with the location where the images of the patient's anatomy were taken.

In other aspects, the collapsed model of the patient's anatomical structure may be a collapsed model of the patient's lungs.

In certain aspects, when executed by the processor, the software application may identify the location of lymph nodes within the patient's lung and generate a lymph node map based on the identified locations of the lymph nodes.

In other aspects, the collapsed model of the patient's anatomical structure may be an anatomical structure selected from the group consisting of the liver, the spleen, the kidney, and the adrenal gland.

BRIEF DESCRIPTION OF THE DRAWINGS

Various aspects and features of the present disclosure are described hereinbelow with references to the drawings, wherein.

DETAILED DESCRIPTION

Figure 1:
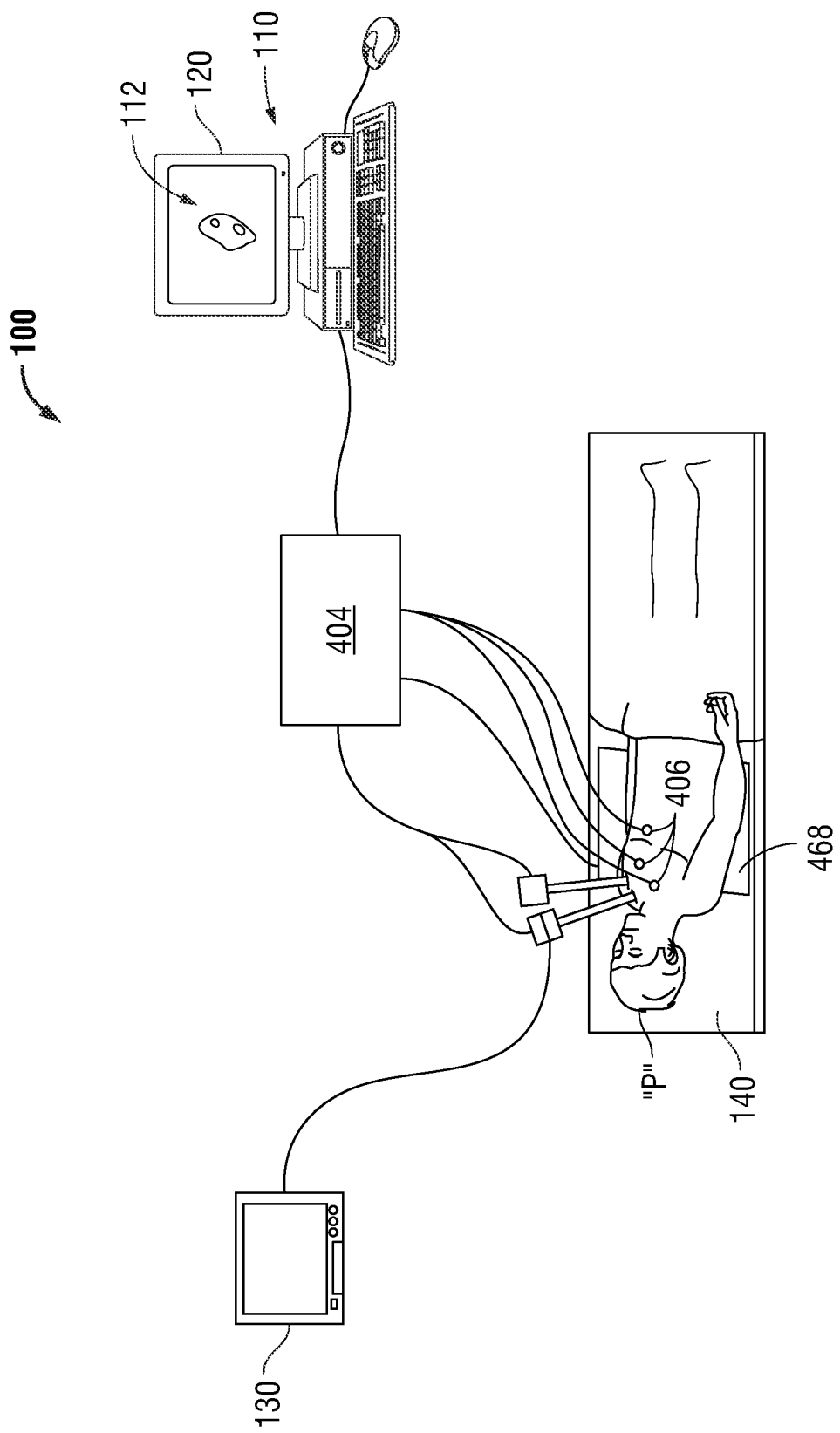
FIG. 1 is a perspective view of a system provided in accordance with the present disclosure configured for providing assistance to a clinician performing surgery.

The present disclosure is directed to methods and systems for providing assistance (e.g., via a user interface of the system) to a clinician performing surgery. The system described herein integrates patient information with intra-operative and post-operative data. The system relates the integrated data to the procedure being performed by the clinician to provide intelligent elucidation of critical decision making factors, such as pre-operative planning and intra-operative and post-operative trends and outcomes. As will be appreciated, the methods and systems described herein enable clinicians to reduce the duration of a surgical procedure and improve surgical outcomes.

Embodiments of the present disclosure are now described in detail with reference to the drawings in which like reference numerals designate corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follow, terms such as front, rear, upper, lower, top, bottom, and similar directional terms are used simply for convenience of description and are not intended to limit the disclosure. In the following description, well-known functions or constructions will be understood by persons skilled in the art and may not be described in detail to avoid obscuring the present disclosure in unnecessary detail.

With reference to FIG. 1, the system includes a computer having a user interface coupled to a Hospital Information System (HIS) to enable the clinician to review patient information. As such, the computer includes a synthesizer which communicates with the HIS either directly or through a cloud computing network via a hardwired connection or wirelessly. Information accessible by the system includes information stored on a Picture Archiving and Communication System (PACS, a Radiology Information System (RIS), an Electronic Medical Records System (EMR), a Laboratory Information System (LIS), and in embodiments, a Cost and Inventory System (CIS), wherein each of which communicates with the HIS, as will be described in further detail hereinbelow.

The system includes a Patient/Surgeon Interface System or Synthesizer that enables the clinician to communicate with the HIS and its associated databases. Using information gathered from the HIS, the clinician is able to identify an Area of Interest ("AOI") illustrating the effects of lung disease, and in embodiments, a software application associated with the synthesizer may be able to automatically identify areas of interest and present these identified areas to the clinician for review via a user interface. Image data gathered from the HIS is processed by the software application to generate a three dimensional (3D) reconstruction of the patient's lungs, and using medical information gathered from the HIS such as, for example, prior surgical procedures, diagnosis of common lung conditions such as COPD, and the location of common structures within the patient's body cavity, the software application generates a model of the patient's lungs in a collapsed state, which forms a Computational Lung Model (CLM) that is displayed to the clinician.

The software application enables the clinician to develop a pre-operative plan around the CLM to achieve an optimal post-surgical outcome. Information from the PACS, EMR, LIS, and other suitable sources of information, such as results of a Pulmonary Function Test (PFT) and other patient vitals, are utilized by the software application to assist the clinician in developing the pre-operative plan. The software application assists the clinician in determining a pathway through which surgical tools may be navigated within the patient's body cavity and optimal locations for access points.

Using information gathered from the HIS and the data gathered and/or generated in the foregoing, the software application suggests incision or resection lines on the patient's lungs to obtain the optimal surgical outcome. The software application displays the incision or resection lines for the clinicians review, and estimates the number of surgical fasteners required to complete the surgical procedure (e.g., surgical staples, surgical clips, etc.) and/or parameters associated with the application of electrosurgical energy (e.g., number of applications, duty cycle, power, duration, etc.) to complete the surgical procedure. In one non-limiting embodiment, the software application estimates the number of surgical cartridges necessary to complete the surgical procedure. Using the incision or resection lines, the software application enables the clinician to selectively remove portions of the patient's lung, at which point the software application estimates the remaining lung volume and respiratory function and presents this information to the clinician. As can be appreciated, after the clinician selects a portion or portions of the patient's lung to remove, the software application updates the estimation of the number of fasteners, electrosurgical energy application, etc. required to complete the procedure.

Once the pre-operative plan has been developed, the software application enables the clinician to virtually perform the surgical procedure. In this way, the clinician is able to rehearse the surgical procedure and/or train clinician staff or other surgeons. The software application enables the clinician to simulate the surgical procedure using a variety of modes, and in particular, a wedge mode, a lobectomy mode, and a segmentectomy mode; each illustrating differing amounts of lung anatomy, as described in further detail hereinbelow with respect to FIGS. 8A, 8B, and 8C.

The clinician determines if the pre-operative plan is satisfactory and, if the clinician is satisfied with the pre-operative plan, the clinician begins the surgical procedure following the steps developed during the pre-operative plan. The software application facilitates the generation of a 3D surface map of the patient's lungs using a thoracoscope having a structured light scanner or other suitable device. The software application displays a plurality of generated 3D surface models of the patient's lungs to the clinician via the user interface such that the clinician is able to select a 3D surface model of the lungs that most accurately depicts the patient's actual anatomy. Using positional data obtained by the structured light scanner, the orientation of the CLM is updated in real time based upon the surgeons view through the thoracoscope camera, and the software application overlays critical structures on the clinician's real-time view of the patient's lungs. The software application displays the CLM to the clinician via the user interface (e.g., a Picture-in-Picture (PIP) view) and illustrates the location of the camera view on the CLM. In certain instances, the software application updates the location of the overlaid critical structures on the CLM as the clinician manipulates portions of the patient's lung. One can appreciate the progress of 3D scanning technology and in this aspect the structured light scanner may be replaced by subsequent means of creating a surface map of the surgical field. The software application enables the clinician to selectively overlay information relating to the surgical procedure on a portion of the user interface. As such, the clinician may choose to display the status of surgical steps determined during pre-operative planning, display information relating to the distance of the surgical instrument relative to critical structures or the AOI within the patient's body cavity, display the patient's vitals, display CT images associated with the location of the real-time view of the patient's lungs displayed on the user interface, display a timer associated with the duration of the surgical procedure, etc.

The software application uses patient information gathered from the HIS to generate a lymph node map, which is presented to the clinician as an overlay of the lymph node map on the CLM. The software application identifies enlarged lymph nodes, assigns identifiers (e.g., colors, intensities, etc.) corresponding to lymph node size, tracks which lymph nodes have been removed by the clinician, and displays this information to the clinician during the surgical procedure. The software application also tracks the status of each surgical step developed in the pre-operative plan, and displays the status of each step to the clinician during the surgical procedure (e.g., completed, pending, etc.).

To assist the clinician in following the pathway generated during pre-operative planning, the software application enables tracking of the surgical instrument within the patient's body cavity using, e.g., VATS, iVATS, or an electromagnetic navigation system. In this manner, the software application displays the location of the distal tip of the surgical instrument relative to critical structures within the patient's body cavity and/or the AOI. If the surgical instrument is approaching critical structures or the AOI, the software application provides warnings and/or decision support to help the clinician guide the surgical instrument to the AOI while avoiding critical structures.

Using information gathered during the surgical procedure, the software application facilitates the generation of a database, which can be stored locally or on the HIS. The database contains information such as, but not limited to, patient data, a comparison of post-operative vitals as compared to predicted post-operative vitals, and enables clinicians to access the data to track trends, simplify pre-operative planning, or other beneficial uses.

Although the systems and methods detailed herein are generally described with respect to the lungs and the thoracic cavity, it is contemplated that the following systems and methods may be applied to any suitable organ or portion of the patient's anatomy (e.g., liver, spleen, kidney, adrenal gland, or the like) and may be applied to other surgical techniques, such as laparoscopic surgeries, bronchoscopic surgeries, and the like.

Referring now to FIG. 1, the present disclosure is generally directed to a system 100 for providing assistance to a clinician performing a surgical procedure. The system 100 includes a computer 110 and a user interface 112 displayed on a suitable display 120 associated with the computer 110 or on any suitable monitoring equipment 130, such as an operating room monitor. It is contemplated that the computer 110 may be any suitable computing device, such as a desktop, laptop, tablet, smartphone, or the like, and in embodiments, the display 120 may be touch sensitive (e.g., capacitive, resistive, surface acoustic wave, or the like), voice activated, or be virtual touch screen compatible. Alternatively, the computer 110 may interface with any suitable user input device, such as a keyboard, a mouse, robotic surgical systems, etc.

Figure 2:
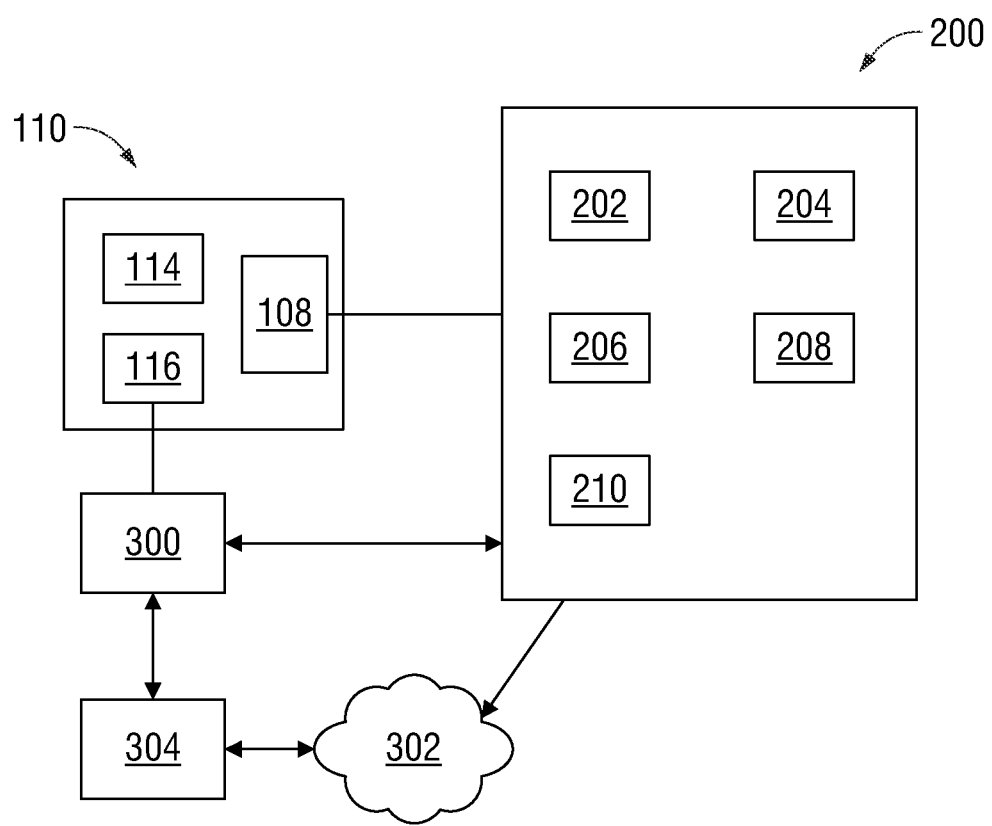
FIG. 2 is a block diagram illustrating the integration of a computer and hospital information system of the system of FIG. 1.

FIG. 2 depicts the integration of the computer 110 with a Hospital Information System (HIS) 200. Although generally described herein as interfacing with the HIS 200, it is contemplated that the computer 110 may interface with any suitable electronic database or systems. The computer 110 includes one or more processors 114 associated with a memory 116. The memory 116 may include any non-transitory computer-readable storage media for storing data and/or software that is executable by the processor 114 (e.g., solid-state, volatile, non-volatile, removable, and non-removable). A network module 108 is coupled to the computer 110 and enables communication between the computer 110 and a network, as will be described in further detail hereinbelow. It is contemplated that the network module 108 may be a hardwired or wireless router and may communicate to the network either through a hardwired connection (not shown) such as optical, RS-232, RS485, SPI/I2C, or the like, or wirelessly using any suitable wireless protocol capable of wirelessly transmitting data either in real time or on demand, such as those conforming to IEEE 802, Zigbee, Bluetooth, or the like.

A software application is stored on the memory 116 and is executable by the one or more processors 114. The software application enables a clinician to access the HIS 200 through the network module 108 via a secured network such as the Health Level-7 (HL7) protocol or the Digital Imaging and Communications in Medicine (DICOM) protocol, although it is contemplated that any suitable protocol may be utilized. As can be appreciated, the software application may be accessed either at a dedicated workstation or remotely via a Virtual Private Network (VPN) accessed using any suitable computing device, such as a laptop, tablet, smartphone, remote workstation, or the like.

With continued reference to FIG. 2, the HIS 200 interfaces with and manages a plurality of databases via a secure network and preferably through the HL7 and DICOM protocols, although it is contemplated that any suitable means of communicating between databases may be utilized. The HIS 200 interfaces with a Picture Archiving and Communication System (PACS) 202, a Radiology Information System (RIS) 204, an Electronic Medical Records System (EMR) 206, a Laboratory Information System (LIS) 208, and in embodiments, a Cost and Inventory System (CIS) 210. It is envisioned that the HIS 200 may interface with any suitable database or management system that may be employed by a hospital. As can be appreciated, communications between the HIS and the plurality of databases are transmitted using the HL7 protocol whereas communications including digital imaging (e.g., medical images) are transmitted using the DICOM protocol.

The PACS 202 stores and/or archives images of various patients obtained using any suitable imaging system (not shown) such as X-ray CT, computerized axial tomography (CAT) scan, positron emission tomography (PET), single-photon emission CT (SPECT), Magnetic Resonant Imaging (MRI), Ultrasound (US), or the like. The RIS 204 complements the HIS 200 and the PACS 202 and serves as an electronic management system for an imaging department of a hospital. In particular, the RIS 204 enables clinicians and support staff to interface with the PACS 202 through the HIS 200 to access digital images of patient's and to associate patient information from the EMR 206 with the digital images stored in the PACS 202. The LIS 208 supports data exchange between a hospital laboratory and the HIS 200, and in particular the EMR 206.

A Patient/Surgeon Interface System or Synthesizer 300 includes a software application that interfaces with the memory 116 and is executable by the one or more processors 114 associated with the computer 110. As described herein, the synthesizer 300 interfaces with the HIS 200 and provides a medium in which the clinician is able to gather patient related data and utilize such data to provide a comprehensive training tool, assist in pre-operative planning, provide intra-operative assistance and intra-operative data collection, assist in post-operative data collection and predict outcome trends, and provide practice improvement data, as will be described in further detail hereinbelow. The synthesizer 300 may communicate directly with the HIS 200 via the intra-net using a hardwired or wireless connection, such as those described hereinabove, or in embodiments, may communicate with the HIS 200 via a cloud computing, such as a synthesizer cloud 302. The synthesizer 300 interfaces with the synthesizer cloud 302 either directly using a hardwired connection or wirelessly through a Virtual Private Network (VPN) 304, such that the synthesizer 300 may access the HIS 200 remotely (e.g., via a device not connected to the intranet).

The synthesizer 300 communicates with the HIS 200 to obtain patient information from the EMR 206. The synthesizer 300 uses the patient information obtained from the EMR 206 to predict, using clinical trends and medical knowledge, the presence of adhesions (either from previous surgeries or radiation treatments), lung deflation capability (from patient pulmonary function measurements and other pulmonary conditions such as COPD, or the like), or other critical features or afflictions that may impact pre-operative planning and/or intra-operative decision making. Using the synthesizer 300, a clinician obtains pre-operative images of the patient from the PACS 202. The pre-operative images, in combination with the patient information obtained from the EMR 206, are used by the synthesizer 300 to construct a volumetric reconstruction of the patient's lungs.

Figure 3:
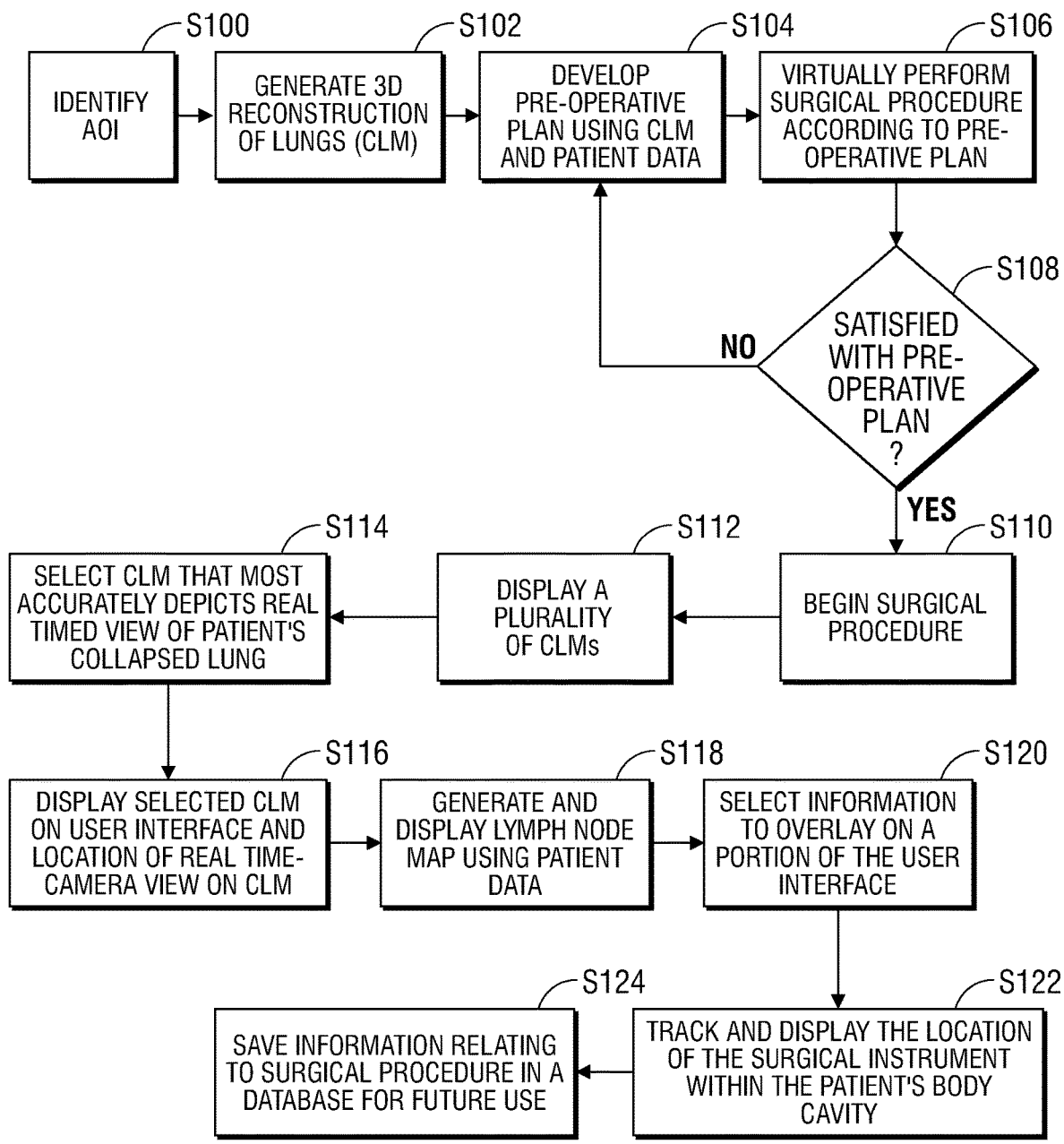
FIG. 3 is a flow chart illustrating a method of performing surgery using the system of FIG. 1.

With additional reference to FIG. 3, a method of performing a surgical procedure with assistance from the synthesizer 300 is described. Specifically, in step S100, the synthesizer 300 enables interactive review of the image data to identify areas of interest ("AM" FIG. 4) illustrating the effects of lung disease (e.g., emphysema, COPD, asthma, cancer, or the like) and assists in determining the location of an AOI within the lungs of the patient either automatically or though input from the clinician.

Several methods of identifying an AOI are contemplated such as ultrasound, CT scan, metabolic scanning, or the like. The results of such methods are stored in the RIS 204 and obtained by the synthesizer from the HIS 200. In one non-limiting embodiment, where the patient "P" is not suffering from easily identified lesions or cancers of the lungs, the results of images generated from a previously acquired CT scan can be analyzed to identify areas of hypodensity. Hypodense portions of the lungs "L" are areas where the density of the tissue is less than the surrounding tissue. This may be particularly useful for clinicians with patients suffering from emphysema as the expanded alveoli or bullae will provide images that have areas which may be substantially darker or blacker than the surrounding tissue, indicating that they are largely air with little to no tissue separating these enlarged alveoli. Because of this hypodensity, image analysis using 3D image processing is particularly useful as identification of the areas where the densities of the images (measured in Hounsfield units of HU) are below a certain threshold (e.g., 950 HU). In an alternative embodiment, PET imaging may be utilized to identify areas of low metabolic activity within the lungs "L" (which should closely correspond to areas of overinflated alveoli. There is very little metabolic activity in these areas because they are mostly comprised of air). As can be appreciated, a device capable of performing a combined PET/CT imaging technique may be utilized. In this way, a PET image set can be utilized to identify the hypodense areas to which navigation and treatment should be directed. After suitable analysis, using one of the above described techniques, the location of the area of interest "AOI" within the lungs "L" may be identified and its location stored in the PACS 202, RIS 204, EMR 206, or within the memory 116 associated with the computer 110.

As will be appreciated, the method of generating a 3D model described herein may be utilized to identify the area of interest "AOI," and in embodiments, the synthesizer 300 may automatically identify areas of interest and present these identified areas of interest to the clinician, at which point the clinician may review each area of interest and select those which require further investigation, either through further studies or through surgical intervention.

In step S102, the synthesizer 300 processes the above mentioned image data and generates a 3D reconstruction of the image data using any suitable method known in the art. In one non-limiting embodiment, the 3D reconstruction is generated using the techniques described in U.S. Patent Application Publication No. 2016/0038248 to Bharadwaj et al. titled "Treatment Procedure Planning System and Method," filed on Aug. 10, 2015, the entire content of which is incorporated by reference herein. As can be appreciated, during a thoracoscopic procedure, such as that described hereinbelow, it is necessary to deflate a portion of the patient's lungs (e.g., induce atelectasis) in order to provide the requisite space within the thoracic cavity for the surgical tools to be maneuvered. As described hereinabove, the 3D reconstruction is necessarily a reconstruction of a fully inflated lung. Therefore, once the surgical procedure has begun, the geometry of the lungs changes leading to a shift in the location of the identified area of interest "AOI" within the lungs and thoracic cavity. Thus, the pre-operative plan that is developed as described in detail hereinbelow must compensate for the altered geometry of the lung during the surgical procedure.

To compensate for this altered geometry, the software application of the synthesizer 300 models the patient's "P" lung "L" in a collapsed state. Specifically, the software application employs a segmentation algorithm to define the boundaries of various types of tissues and group together similar types of tissue based on their density and continuity, amongst other factors. It is contemplated that the software application may utilize any suitable segmentation algorithm known in the art, such as binary masking, determination of the optimum threshold that separates tissue and background, adaptive region growing, wavefront propagation, or the like. In one non-limiting embodiment, the software application may utilize any of the segmentation techniques described in U.S. Patent Application Publication No. 2016/0038248 to Bharadwaj et al., previously incorporated by reference hereinabove.

As can be appreciated, the synthesizer 300 may not be able to differentiate all of the differing tissue types. As such, the software application enables selective toggling of arteries, veins, bronchi, and the like to correct any inaccuracies. In this manner, the software application presents each segmented group as a different color or different transparency level that may be selectively adjusted by the clinician in order to enable the clinician to better identify each segmented or differentiated group, or in embodiments, may present identified structures as opaque and unidentified structures as translucent, or vice versa.

To further enhance the accuracy of the reconstruction of the collapsed lung, the software application of the synthesizer 300 adjusts the 3D reconstruction to account for the effect of gravity (e.g., the orientation of the patient on the operating table 140) and the curvature of the patient's spine in the coronal or frontal plane (e.g., the plane dividing the patient's "P" body into ventral and dorsal sections). Other structures within the thoracic cavity affect lung volume and placement of the lungs within the patient's thoracic cavity, such as adhesions, lesion, of the like. The software application recognizes such structures via the images obtained by the synthesizer 300 from the PACS 202 and accounts for the presence of these structures by forcing the lung "L" to sit higher in the thoracic cavity, in the case of the presence of an adhesion, by fixing the adhesions to a fixed boundary at the ribcage and applying elastic models to determine displacement, or combinations thereof. In the alternative, the software application may recognize the removal of adhesions, or removal of the adhesions may be manually entered into the synthesizer by the clinician, and the software application will readjust the model accordingly (e.g., the lung "L" will sit further down towards the helium).

The synthesizer 300 accesses the EMR 204 to estimate a more likely level of lung deflation as the elastic properties of the lung tissues will be affected by common lung conditions such as COPD, the age of the patient, smoking status of the patient, etc. Additionally, the synthesizer 300 obtains information from the EMR 204 regarding any prior surgical procedures the patient "P" may have undergone that would impact overall lung volume. After identifying the various structures within the lung "L," the software application employs a Finite Element Analysis algorithm to model the lung "L" and present the collapsed lung model to the clinician on the display 120. The resulting 3D model of the collapsed lung forms a Computational Lung Model (CLM) that is the 3D model that is displayed to the clinician on the display 120 or monitoring equipment associated with the computer 110 during pre-operative planning, intra-operative assistance, and post-operative review.

For a detailed description of an exemplary system for modeling a collapsed lung, reference can be made to U.S. patent application Ser. No. 16/045,996, to Sartor et al. titled "Modeling a Collapsed Lung Using CT Data," filed Jul. 26, 2017, the entire content of which is incorporated by reference herein.

Once the CLM has been developed, in step S104 (FIG. 3) the software application enables a clinician to formulate a pre-operative plan, and in particular, a pre-operative plan that achieves an optimal or desired post-surgical outcome, using information from the PACS 202, EMR 204, LIS 206, and any other suitable source of patient information, such as vitals checked before the surgical procedure or the like (e.g., Pulmonary Function Tests (PFT's) such as Forced Expiratory Volume in the first one second of expiration ($FEV_1$), Forced Vital Capacity (FEC), Total Lung Capacity (TLC), Functional Residual Capacity (FRC), etc.).

The software application of the synthesizer 300 assists a clinician in determining a pathway through which the surgical tools used to treat the area of interest "AOI" may be advanced within the patient "P." Additionally, the software application may identify an optimal location at which a trocar or port may be introduced to most easily reach the area of interest "AOI" using a surgical tool 400 (FIG. 1) and/or a thoracoscope 510 and determines an angle at which the surgical tool should be introduced within the body cavity to avoid contacting obstructions (e.g., bones or the like) or critical structures (e.g., organs, veins, arteries, etc.). In embodiments, the software application may assist the clinician in selecting a surgical tool that is best suited to treat the area of interest "AOI."

Figure 4:
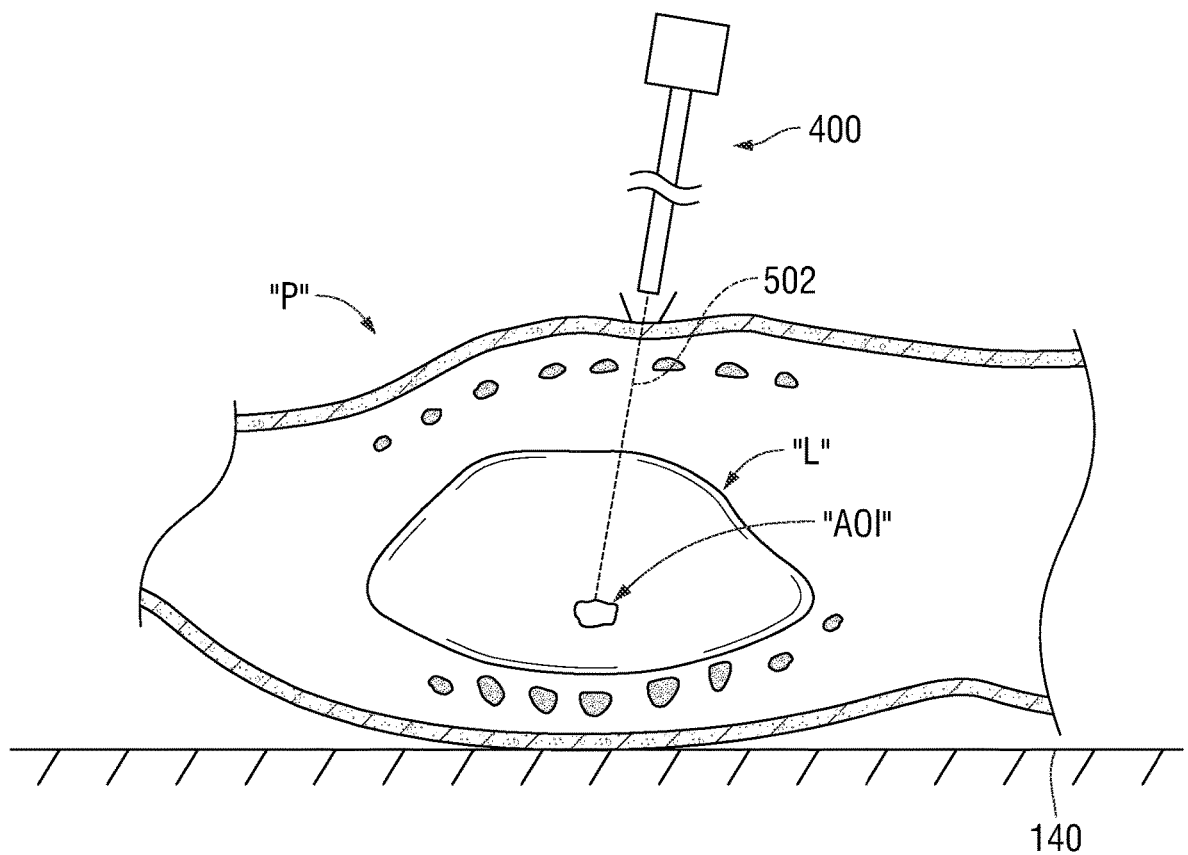
FIG. 4 is a cross-sectional view of the patient's thoracic cavity showing a pathway for a surgical instrument to an area of interest within the patient's lungs.

With reference to FIG. 4, the software application enables the clinician to virtually navigate the surgical tool 400 into and within the modeled thoracic cavity. The software application highlights or otherwise illustrates the pathway 502 in which the surgical tool 400 and/or the thoracoscope 510 follows within the modeled thoracic cavity in the user interface, and in embodiments, may suggest alternative pathways to optimize navigation of the surgical tool 400 within the thoracic cavity. It is contemplated that the software application may prompt the clinician to select a suggested pathway 502 or ignore the suggestion and permit the clinician to continue plotting a custom pathway.

Figure 5:
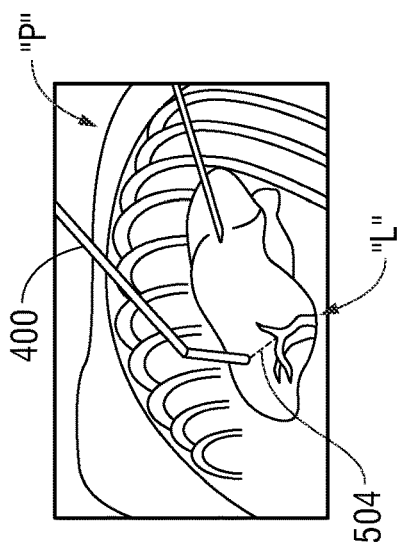
FIG. 5 is an illustration of the user interface of the system of FIG. 1, displaying a cross-sectional view of the patient's thoracic cavity showing a surgical tool and a thoracoscope advanced therein.

The software application of the synthesizer 300 facilitates the virtual placement of incision lines 504 (FIG. 5), resection lines, etc. on the CLM, which are illustrated on the CLM using a dashed line or any other suitable means for illustrating the incision lines 504 within the user interface 112. Once the clinician places the incision lines 504 on the CLM, the software application estimates the number of fasteners required to complete close the incision and/or to complete the surgical procedure (e.g., surgical staples, surgical clips, sutures, mesh, etc.). In embodiments, the software application may estimate the number of times electrosurgical energy is required to be applied, the duration at which the electrosurgical energy should be applied, etc. In one non-limiting embodiment, the software application estimates the number of surgical cartridges necessary to complete the surgical procedure.

Figure 7:
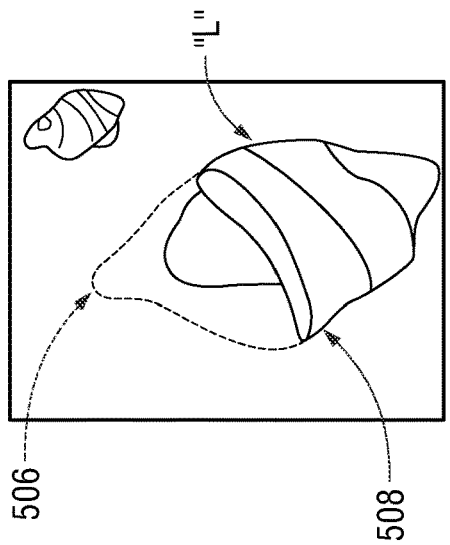
FIG. 7 is an illustration of the user interface of the system of FIG. 1, displaying a model of the patient's lung showing a plurality of user defined lung volumes and a segment portions of the patient's lung that has been selectively removed.
Figure 6:
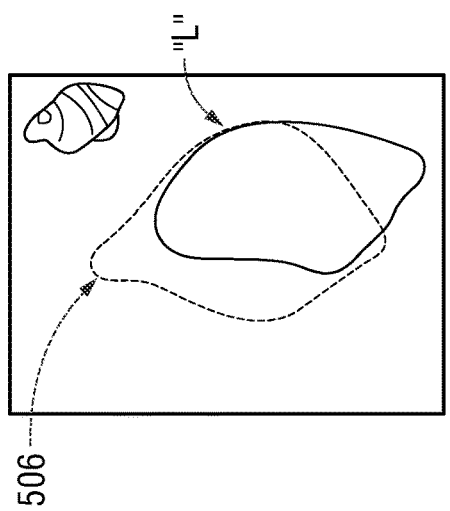
FIG. 6 is an illustration of the user interface of the system of FIG. 1, displaying a model of the patient's lung showing a portion of the patient's lung that has been selectively removed.

In a similar manner to developing a suggested pathway for the surgical tool 400 within the thoracic cavity, the software application suggests alternative incision or resection lines based upon information gathered from the EMR 204. It is envisioned that the clinician may select an alternative suggested by the software application or disregard the prompt altogether. In embodiments, the clinician may place a plurality of incision lines on the CLM to define a plurality of discreet lung volumes to resect, such as a first lung volume 506, a second lung volume 508, etc. (FIGS. 6 and 7). The software application analyzes the placement of the incision lines 504 on the CLM and identifies potential issues with their placement based upon information gathered from the EMR 204 or based upon general medical knowledge regarding sensitive formations and/or vasculature within the lung. As can be appreciated, this general medical knowledge may be stored as data within the memory 116, a local area network, the EMR 204, or the like.

Using the plurality of lung volumes defined by the clinician on the CLM, and using patient information gathered from the HIS 200, the software application estimates the remaining lung volume and/or respiratory function parameters of the lungs after the selected portion of the lung is removed (e.g., $FEV_1$, FVC, TLC, FRC, etc.). As illustrated in FIGS. 6 and 7, the software application displays the CLM on the user interface and illustrates each clinician defined lung volume and/or the lung volumes suggested by the software application thereon using shading, coloring, differentiated lines (e.g., dashed, solid, or the like). In this manner, each lung volume can be easily identified by the clinician, at which point the clinician is able to select which lung volume to remove. The software application displays information pertaining to the patient's lungs, such as $FEV_1$ or the like, and updates the information as the clinician removes selected portions of the lung in the user interface. In particular, the software application displays information relating to which portion of the lung has been removed and predicted post-operative lung function. In one non-limiting embodiment, the software application displays the removed lung volume in phantom (e.g., dashed lines) at one portion of the user interface (e.g., at a center portion), a depiction of the CLM with the defined lung volumes at another portion of the user interface (e.g., at a corner or the like), the lung volume being removed (e.g., upper lobe), and the predicted post-operative $FEV_1$. It is contemplated that the clinician may selectively choose each lung volume in an iterative manner, or in any suitable manner, such that the clinician may determine how much lung volume to remove to achieve the desired post-operative results.

Figure 8C:
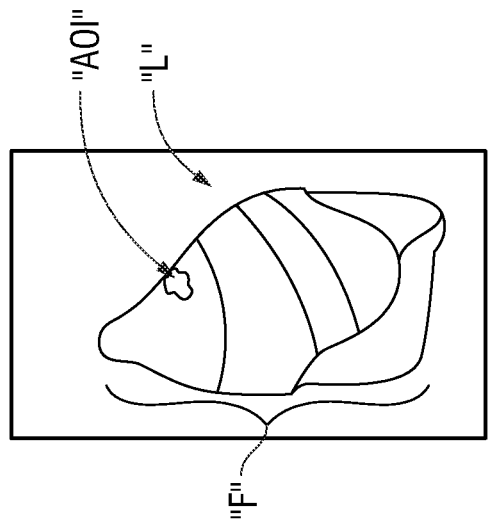
FIG. 8C is an illustration of the user interface of the system of FIG. 1, displaying the patient's lung with anatomy associated with a wedge training module.
Figure 8B:
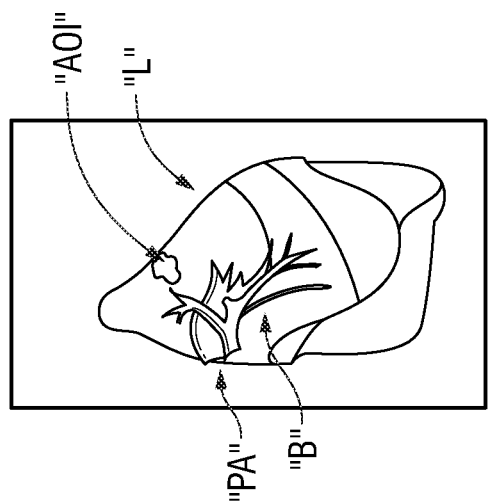
FIG. 8B is an illustration of the user interface of the system of FIG. 1, displaying a model of the patient's lung with anatomy associated with a segmentectomy training module.
Figure 8A:
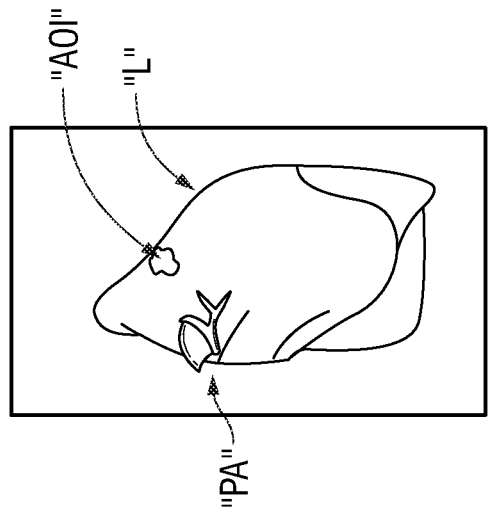
FIG. 8A is an illustration of the user interface of the system of FIG. 1, displaying a model of the patient's lung with anatomy associated with a lobectomy training module.

Turning to FIGS. 8A, 8B, and 8C, once pre-operative planning is complete, in step S106 (FIG. 3), the software application of the synthesizer 300 includes a module for simulating the surgery, such that the clinician may rehearse the surgical procedure, train, or train clinical staff or other surgeons. To enable more detailed analysis and more comprehensive training/rehearsing, the module includes a plurality of modes, each showing a differing amount of lung anatomy. In particular, the module includes a lobectomy mode (FIG. 8A), a segmentectomy mode (FIG. 8B), and a wedge mode (FIG. 8C), although other modes are contemplated. The lobectomy mode illustrates lesions, nodules, lobes, fissures, and main lobar branches of the pulmonary artery, pulmonary vein, and/or bronchus, and combinations thereof ("PA"). The segmentectomy mode illustrates lesions, nodules, fissures, segments in the lobe of interest, lobar branches of the pulmonary artery, pulmonary vein, and/or bronchus in the lobe of interest, segmental branches of the pulmonary artery, pulmonary vein, and/or bronchus, or combinations thereof for highlighted segments in the lobe of interest ("B"). The wedge mode illustrates lesions, nodules, fissures, segments surrounding the lesion in the lobe of interest (e.g., upper lobe, lower lobe, etc.), and combinations thereof ("F"). After virtually performing the planned surgical procedure, in step S108, the clinician determines if the pre-operative plan is satisfactory. If the clinician determines that the pre-operative plan is not satisfactory, the clinician re-enters the pre-operative planning phase and makes any necessary adjustments. At this point, the clinician may again virtually perform the surgical procedure using the modified pre-operative plan. On the other hand, if the clinician determines that the pre-operative plan is satisfactory, in step S110, the clinician begins the surgical procedure using the pre-operative plan developed during pre-operative planning. As can be appreciated, it is contemplated that simulating the surgical procedure may be optional such that the clinician may choose to begin the surgical procedure without initially simulating the surgical procedure. In this manner, the clinician may proceed from step S104 to step S108, or in embodiments, from step S104 to step S110 to begin the surgical procedure.

During an intra-operative portion of the procedure, the clinician inserts a trocar or trocars (not shown) into the patient at the pre-determined locations identified during pre-operative planning, through which the surgical instrument 400 (e.g., forceps, surgical stapler, electrosurgical instrument, clip applier, or the like) is advanced and into the patient's body cavity. As can be appreciated, a second surgical tool is advanced within the body cavity of the patient to capture real-time images of the patient's anatomy during the surgical procedure. In one non-limiting embodiment, the second surgical tool is the thoracoscope 510 or other suitable device, such as an endoscope or laparoscope, capable of being advanced within the thoracic cavity of a patient "P" and having a structured light scanner 512 (FIG. 9) disposed thereon. It is contemplated that the thoracoscope 510 may include any suitable structured light scanner 512 known in the art, such as an LED or LED infrared laser, or a visible light LED laser, that is disposed in a suitable manner on the thoracoscope 510 to scan a pattern (line, mesh, or dots), by rotating mirror, beam splitter, or diffraction grating, or may be a digital light processing (DLP) projector. In one non-limiting embodiment, the structured light scanner 512 is an LED laser having collimated light. The thoracoscope 510 further includes an IR camera 514 (FIG. 9) disposed thereon that is capable of detecting IR light. It is contemplated that the IR camera 514 may be thermographic camera known in the art, such as ferroelectric, silicon microbolometer, or uncooled focal plane array (UFPA). It is further contemplated that the various sensors disposed on the thoracoscope 510 may be separate and distinct components with associated hardware and/or software, or may be part of a commercial platform such as Intel®'s Real Sense™. The thoracoscope 510 is a steerable thoracoscope capable of being manipulated relative to a longitudinal axis defined through proximal and distal portions of the thoracoscope 510, such that a distal portion of the thoracoscope 510 can be oriented at various angles relative to the patient's "P" lungs (FIG. 10). As can be appreciated, a steerable thoracoscope is capable of capturing the required images of the patient's "P" lungs without being removed from the patient's "P" body cavity. In contrast, if the thoracoscope 510 is a rigid thoracoscope, it may be necessary to advance the rigid thoracoscope through multiple incisions or trocars in order to take the necessary images of the patient's "P" lungs to generate the 3D surface model of the patient's "P" lungs.

For a detailed description of an exemplary thoracoscope or endoscope having a structured light scanner, reference may be made to U.S. patent application Ser. No. 15/468,981, filed on Mar. 24, 2017, entitled THORACIC ENDOSCOPE FOR SURFACE SCANNING to Sartor et al., the entire content of which is incorporated herein by reference.

Figure 11A:
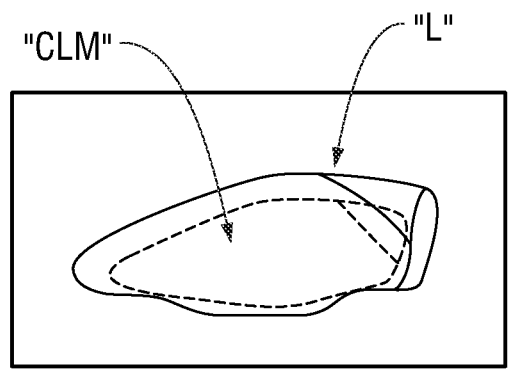
FIG. 11A is an illustration of the user interface of the system of FIG. 1, displaying the patient's lung in a collapsed state, with a 3D model of the collapsed lung overlaid thereon.
Figure 11B:
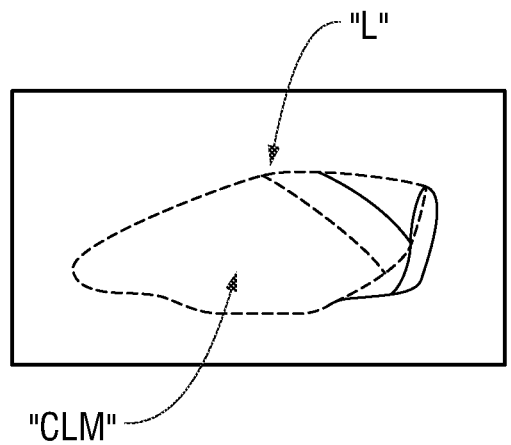
FIG. 11B is an illustration of the user interface of the system of FIG. 1, displaying the patient's lung in a collapsed state, with another 3D model of the collapsed lung overlaid thereon.
Figure 11C:
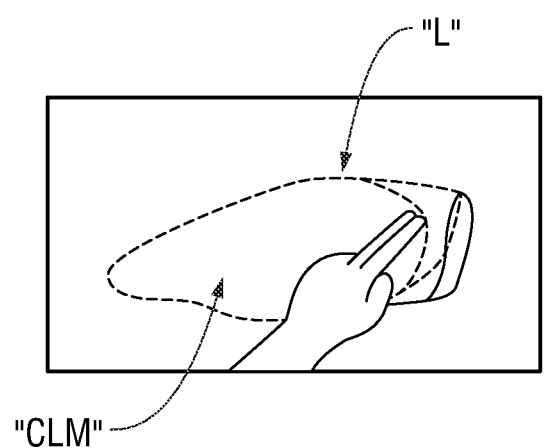
FIG. 11C is an illustration of the user interface of the system of FIG. 1, displaying the patient's lung in a collapsed state, with yet another 3D model of the collapsed lung overlaid thereon.

Using the information gathered by the thoracoscope 510, the software application of the synthesizer 300 generates a 3D surface model of the patient's "P" collapsed lung. The 3D surface model of the collapsed lung is utilized by the software application to update the CLM and provide a more accurate model of the patient's "P" lungs "L" in the collapsed state. In step S112 (FIG. 3), the software application displays a plurality of generated 3D surface models of the patient's lungs to the clinician via the user interface 112. In step S114, the software application enables the clinician to select a lung deflation model that most accurately depicts the patient's "P" lung "L" in the collapsed state (FIGS. 11A, 11B, and 11C). For example, FIG. 11A illustrates the CLM superimposed over the scan of the patient's lung in the collapsed state. FIG. 11B illustrates a selected CLM that most accurately matches the scan of the patient's lung in the collapsed state. FIG. 11C illustrates the clinician using hand gestures to alter the shape of the CLM to more closely match the scan of the patient's lung in the collapsed state.

Figure 9:
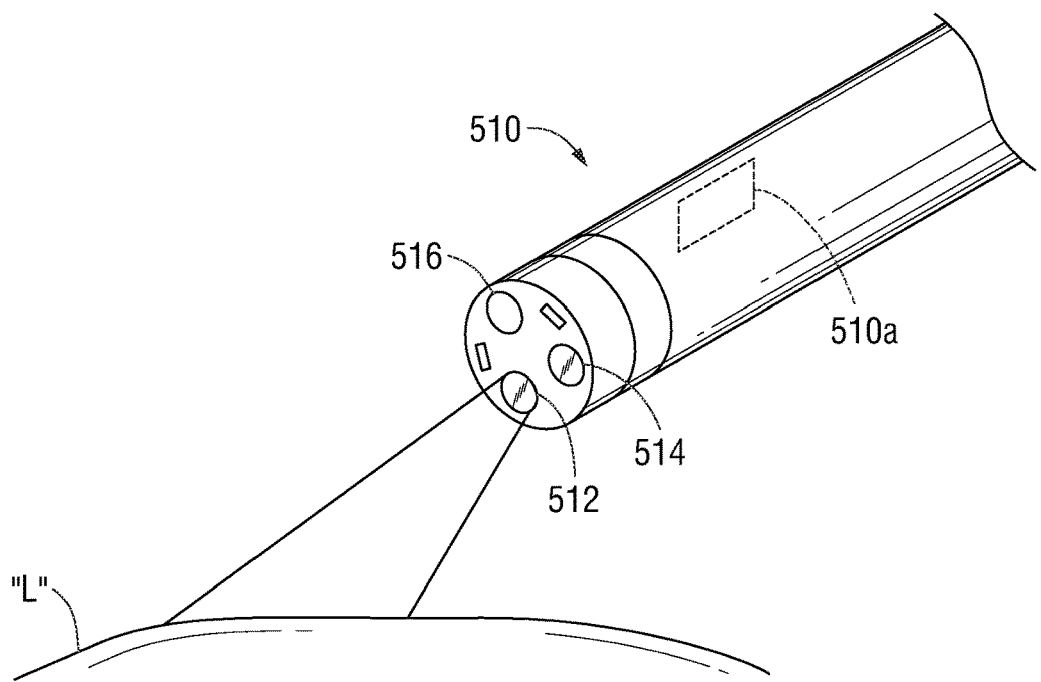
FIG. 9 is a perspective view of a thoracoscope provided in accordance with the present disclosure having a structured light scanner disposed thereon.
Figure 10:
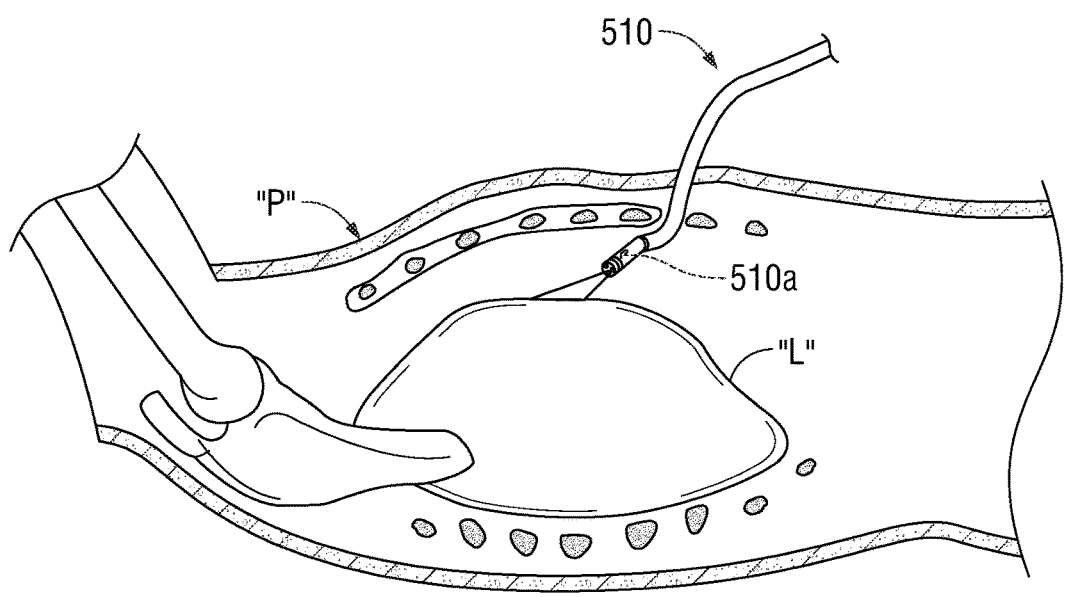
FIG. 10 is a side, cross-sectional view of the patient's thoracic cavity showing the thoracoscope of FIG. 9 advanced therein.

With reference to FIG. 9, it is further contemplated that, rather than comparing the CLM to the scan obtained by the structured light scanner 512, the CLM may be compared to the clinician's real-time view of the patient's "P" collapsed lung "L" obtained by the thoracoscope 510. In this manner, the thoracoscope 510 includes a camera 516 or other suitable device for capturing video images disposed at a distal portion thereof. As can be appreciated, the thoracoscope 510 may be any suitable thoracoscope capable of being used during a VATS procedure or iVATS procedure. In embodiments, the camera 516 may be an optical scanning system (not shown), such as a DLP system, that may be utilized to accurately size the patient's "P" lung "L" in the collapsed state.

Figure 12:
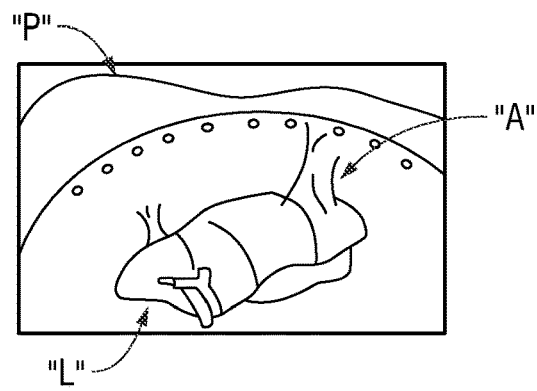
FIG. 12 is an illustration of the user interface of the system of FIG. 1, displaying a cross-sectional view of a 3D model of the patient's thoracic cavity showing the lungs and adhesions attached thereto.

Using positional data obtained by the structured light scanner 512, or the optical scanning system, various feature points or fiducials are detected within the structured light scanner data, such as fissures, ligament attachments, adhesions "A," the surface height of the patient's "P" lungs "L," or any other suitable feature point located within the thoracic cavity (FIG. 12). Once the feature points are identified, the offset of these detected feature points relative to corresponding feature points in the collapsed CLM is calculated. It is contemplated that the offset of the feature points between the structured light scanner data and the CLM data may be calculated using any suitable feature matching algorithm, such as Scale-Invariant Feature Transform (SIFT), Rotation-Invariant Feature Transform (RIFT), Generalized Robust Invariant Feature (G-RIF), Speeded Up Robust Features (SURF), Principal Component Analysis SIFT (PCA-SIFT), Gradient Location-Orientation Histogram (GLOH), Gauss-SIFT, or the like. The software application uses the calculated offsets of the feature points and regenerates the CLM to more accurately reflect the observed condition of the patient's "P" collapsed lung "L." As can be appreciated, the CLM can be regenerated in real time as the thoracoscope 510 is advanced within the thoracic cavity relative to the patient's "P" lung "L." In this manner, the software application of the synthesizer 300 monitors the location of visual landmarks, such as fissures, lesions, or the like, or may use internal landmarks such as nodules (identifiable through the use of lesion detection technology) or fiducials (not shown) that have been previously placed within the patient's "P" lung "L." In embodiments, the software application may detect a lesion within the patient's "P" lung "L" and treat the lesion as a natural fiducial, such that critical structures within the patient's "P" lung "L" can be identified within the CLM.

For a detailed description of updating a patient's collapsed lung using a structured light scanner, reference can be made to U.S. patent application Ser. No. 16/045,996, previously incorporated by reference hereinabove.

Figure 13:
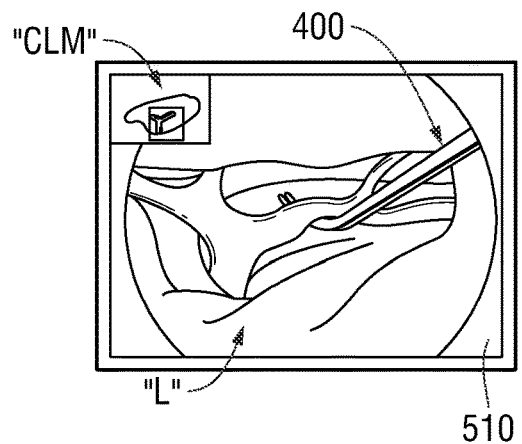
FIG. 13 is an illustration of the user interface of the system of FIG. 1, showing a camera view from the thoracoscope of FIG. 9 and a picture-in-picture view of the 3D model of the collapsed lung overlaid thereon.
Figure 14:
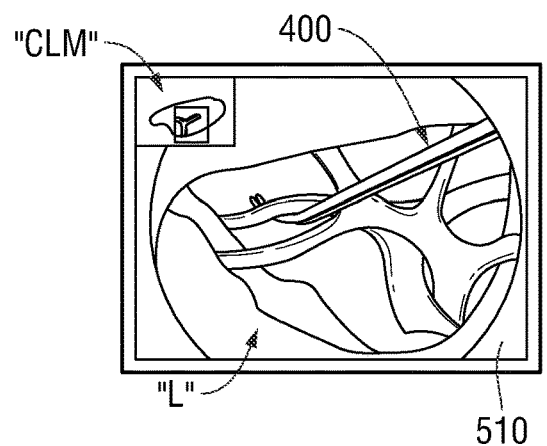
FIG. 14 is another illustration of the user interface of the system of FIG. 1, showing a camera view from the thoracoscope of FIG. 9 and a picture-in-picture view of the 3D model of the collapsed lung overlaid thereon.

As the thoracoscope 510 is advanced within the thoracic cavity, video images are captured and transmitted to the monitor associated with the computer 110 or the monitoring equipment 130 (FIG. 1), providing a real time view of the patient's "P" collapsed lung "L." The 3-D model of the collapsed lung is superimposed over the real-time view of the lungs "L," such that the lesion and other structures inside the lung "L" are illustrated in the real-time view to enable the clinician to more accurately treat the area of interest "AOI" and avoid critical structures located within the lung "L." As illustrated in FIGS. 13 and 14, in step S116 (FIG. 3) it is contemplated that the software application may illustrate the CLM upon the clinician's request as a picture-in-picture (PIP) view or on the side of an operating room monitor. Alternatively, the illustration of the CLM may be displayed as a side-by-side view, or the like, depending upon the needs of the clinician performing the procedure. The PIP illustration of the CLM shows where the camera view of the thoracoscope 510 is located on the CLM.

Figure 15:
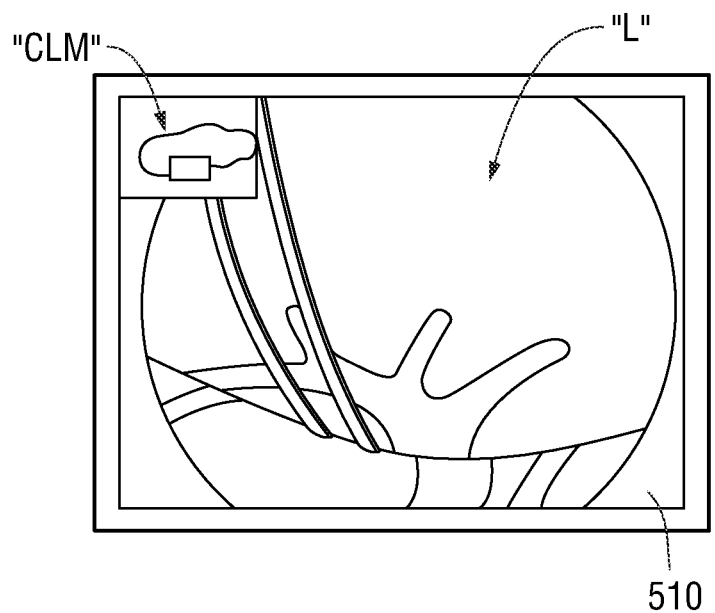
FIG. 15 is an illustration of the user interface of the system of FIG. 1, showing critical structures within the lung that have been overlaid on the camera view from the thoracoscope of FIG. 9.
Figure 16:
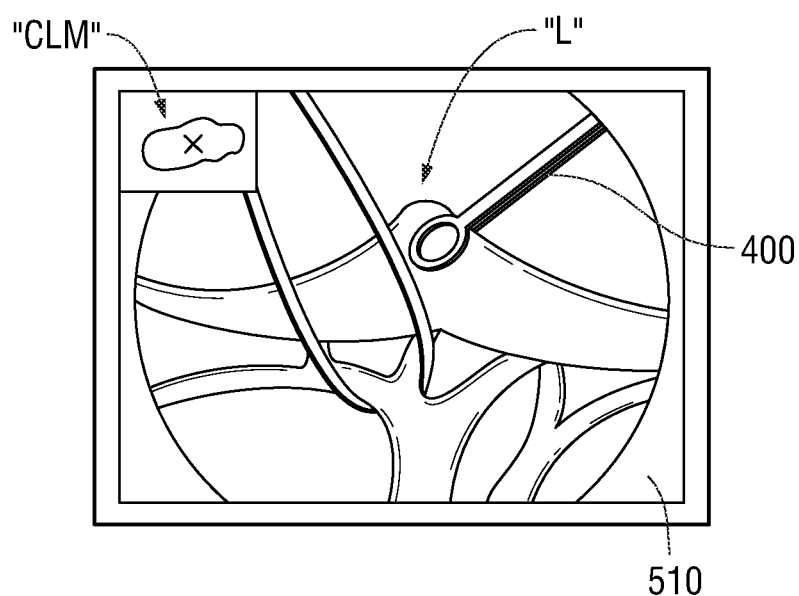
FIG. 16 is an illustration of the user interface of the system of FIG. 1, showing the camera view from the thoracoscope of FIG. 9 with the clinician manipulating the patient's lung.

As can be appreciated, with reference to FIGS. 15 and 16, anatomical features of the patient's "P" lung "L" that have been reconstructed in the CLM can be displayed in the correct location relative to the camera view of the thoracoscope 510 when the patient's "P" lung "L" is in a resting position within the thoracic cavity (e.g., not manipulated by the clinician using forceps or the like). In this manner, the lung "L" must be in the position previously recognized and matched by the software application through the fiducials, landmarks or fissures, and/or coordinates generated by instrument tracking (such as an electromagnetic tracking system, as will be described in further detail hereinbelow). If the lung "L" is manipulated by the clinician using a tool or device such as surgical instrument 400, the PIP illustrating the CLM will be shown as being unavailable (such as with an X or other identifying means) until the lung "L" is returned to its previous condition.

In embodiments, the software application of the synthesizer 300 uses an optical scanner (not shown), such as the DLP system described hereinabove, to evaluate lung and hilar structures of the lung "L" as it is manipulated by the clinician and associates the lung and hilar structures as 3D surfaces. The software application identifies offsets from the 3D lung and hilar structures from corresponding lung and hilar structures of the CLM, applies the identified offsets as displacements, and regenerates the CLM to correspond to the real time orientation of the lung "L." In particular, the software application can model bending of vessels and airways within the lung "L" from how they are bent at the hilum and reconstruct the model of the deflated lung parenchyma surrounding such structures within the CLM.

Figure 17:
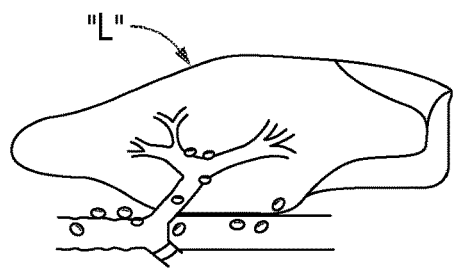
FIG. 17 is an illustration of the user interface of the system of FIG. 1, showing a map of a lymph node system of the patient's lung overlaid on the 3D model of the collapsed lung.
Figure 18:
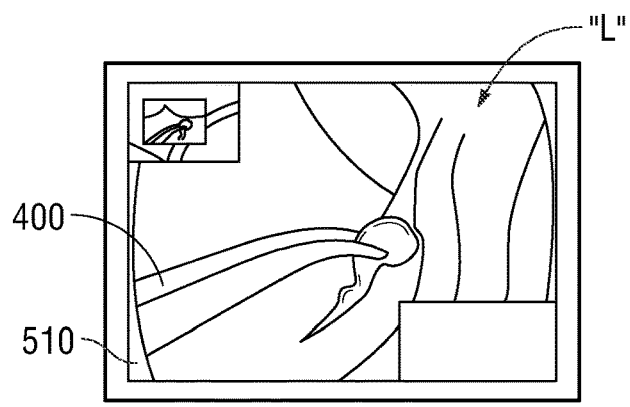
FIG. 18 is an illustration of the user interface of the system of FIG. 1, showing a camera view from the thoracoscope of FIG. 9 as a clinician removes a lymph node from the lung.

With reference to FIGS. 17 and 18, in step S118 (FIG. 3) using patient information gathered from the HIS 200, the software application reconstructs a lymph node map from CT images stored within the PACS 202. In particular, the software application predicts the location of each lymph node within the CLM using a variety of known anatomical situations and generates a plurality of lymph node maps. The software application presents each lymph node map to the clinician through the user interface 112, at which time the clinician selects the lymph node map that most closely resembles the patient's "P" actual anatomy. The selected lymph node map is overlaid on the CLM and identifies enlarged lymph nodes using any suitable means, such as through images obtained through the HIS 200, through patient information stored on the EMR 204, etc. In one non-limiting embodiment, the software application assigns colors to each lymph node corresponding to, e.g., the lymph node size, whether it is enlarged or not, etc. In embodiments, the software application identifies an enlarged lymph node and presents a text box 520 or other similar feature titled "Enlarged Lymph Node" or the like and identifying the number assigned to the lymph node (FIG. 20). The software application further recognizes which lymph nodes have been removed and displays this information to the clinician in the user interface 112 (FIG. 18). For a detailed description of tracking lymph node specimens, reference can be made to U.S. Provisional Patent Application No. 62/508,724, to Sartor et al., tiled "Systems, Devices, and Methods for Lymph Specimen Tracking, Drainage Determination, Visualization, and Treatment," filed May 19, 2017, the entire content of which is incorporated by reference herein.

Figure 19:
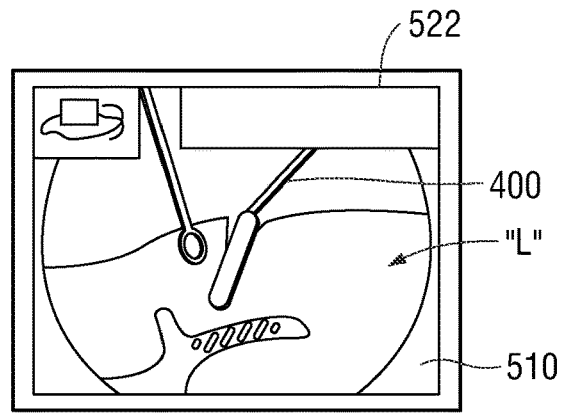
FIG. 19 is an illustration of the user interface of the system of FIG. 1, showing a camera view from the thoracoscope of FIG. 9 as the clinician performs a surgical procedure and a text box indicating the status of surgical procedures developed during pre-operative planning.

In step S120 (FIG. 3) the software application of the synthesizer 300 monitors completion of each surgical step identified within the pre-operating plan. In particular, the software application monitors which branches have been divided or if a leak test has been completed through user gesture recognition, by tactile feedback through the surgical instrument 400 or on the user interface 112, or any other suitable means for identifying whether a surgical step has been completed. In embodiments, the software application displays the surgical steps to be completed, the status of the surgical step (e.g., undivided, divided, ligated, etc.), the time at which the surgical step was completed, the duration of time it took to complete each surgical step, etc. (FIG. 19) in a text box 522 or any other suitable fashion. Although generally illustrated as being displayed at an upper corner of the display screen 120, it is contemplated that the surgical step information may be displayed at any location within the display screen 120 such that the clinician may readily observe the status of each step, but not have an impeded view of the images captured by the thoracoscope 510 (FIG. 19). The software application enables the clinician to capture still-shots (e.g., images) and/or video images during selective portions of the surgical procedure and store the images and videos in the memory 116 associated with the computer 110. It is contemplated that the software application associates each image or video with the time at which the image was captured (e.g., applies a time stamp). In embodiments, the clinician may selectively fast forward, rewind, or otherwise replay the captured videos in real time speed or in slow motion.

Figure 20A:
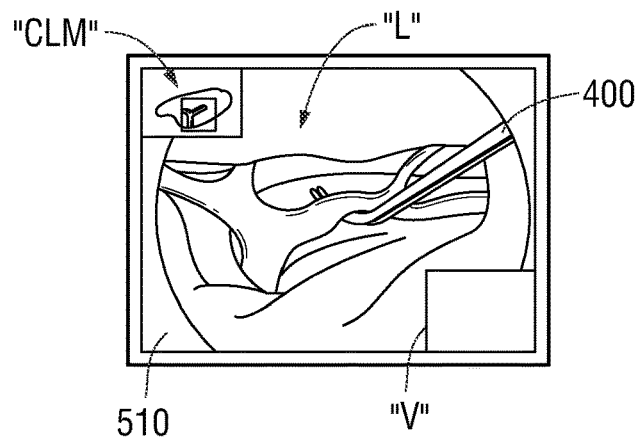
FIG. 20A is an illustration of the user interface of the system of FIG. 1, showing a camera view from the thoracoscope of FIG. 9 and the patient's vitals overlaid thereon.
Figure 20B:
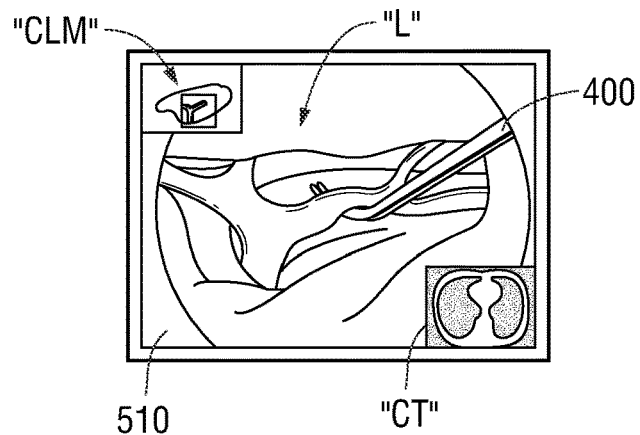
FIG. 20B is an illustration of the user interface of the system of FIG. 1, showing a camera view from the thoracoscope of FIG. 9 and CT images associated with the patient overlaid thereon.
Figure 20C:
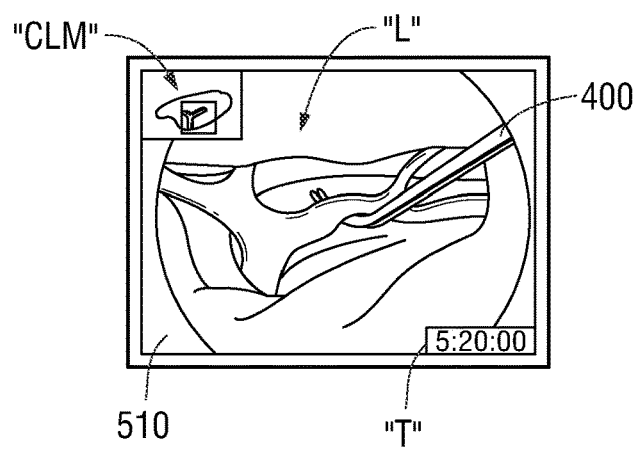
FIG. 20C is an illustration of the user interface of the system of FIG. 1, showing a camera view from the thoracoscope of FIG. 9 and a time associated with the surgical procedure overlaid thereon.

In step S122 (FIG. 3), the location of the thoracoscope and/or the surgical instrument 400 is tracked using VATS or iVATS, or in embodiments, tracking of the thoracoscope 510 and/or the surgical instrument 400, and thereby the camera view, may be achieved through tracking of pre-inserted fiducials (not shown) or other pre-identified visual landmarks within the thoracic cavity and correlating their position within the thoracic cavity to the corresponding location in the CLM. In embodiments, it is contemplated that the software application may track the position of the surgical instruments 400 distal tip relative to the patient's "P" lung "L" or the AOI. During tracking of the distal tip of the surgical instrument 400, the relative location of the distal tip of the surgical instrument 400 relative to the lesion (e.g., distance the distal tip is from the lesion) or other critical structures may be displayed on the display screen 120 (FIG. 1). It is contemplated that additional information pertaining to the location of the distal tip of the surgical instrument 400 relative to the lesion or other critical structures may be presented on the display screen 120, such as images obtained from the HIS 200 or PACS 202, real-time intra-operative ultrasound images obtained from the surgical instrument 400, the patient's vitals (such as those obtained from anesthesia monitoring equipment), a timer, or the like (FIGS. 20A, 20B, and 20C). Specifically, FIG. 20A illustrates an overlay of the patient's vitals "V", such as those taken for anesthesia, on the real-time view of the patient's lungs. FIG. 20B illustrates a CT image "CT" overlaid on the real-time view of the patient's lungs to provide additional detail regarding the anatomy of the specific portion of the patient's lungs that the clinician is treating. In another embodiment, FIG. 20C illustrates a timer "T" or other similar means for displaying elapsed time (e.g., the total duration of the procedure) to the clinician during the surgical procedure. As can be appreciated, the clinician may selectively access each display during the surgical procedure as desired.

For a detailed description of displaying medical images on a display during a surgical procedure, reference can be made to U.S. patent application Ser. No. 15/585,592 to Rossetto et al., titled "Medical Image Viewer Control from Surgeon's Camera," filed May 3, 2017, the entire content of which is incorporated by reference herein.

Figure 21:
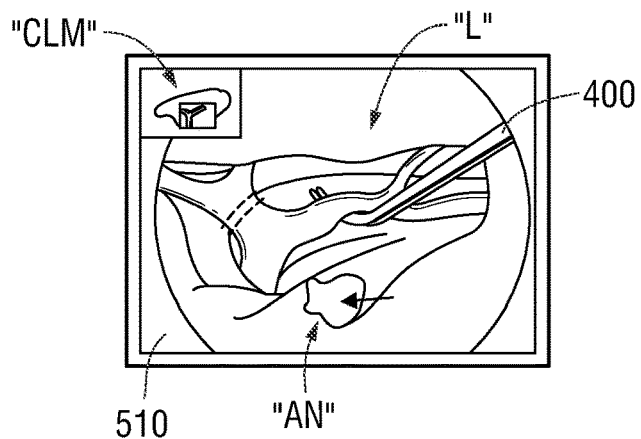
FIG. 21 is an illustration of the user interface of the system of FIG. 1, showing a camera view from the thoracoscope of FIG. 9 and an area of interest drawn on the camera view by the clinician.
Figure 22:
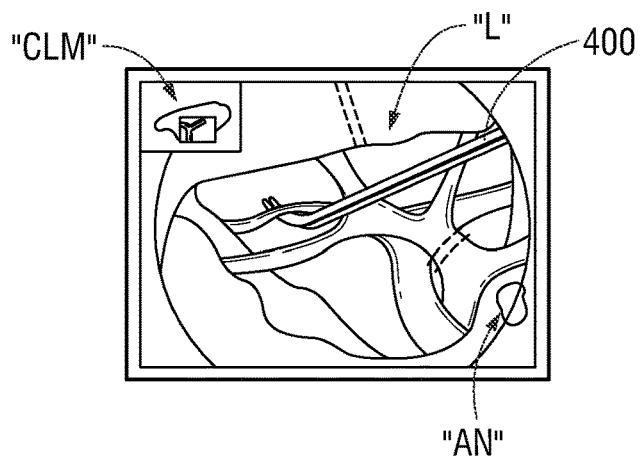
FIG. 22 is an illustration of the user interface of the system of FIG. 1, showing a camera view from the thoracoscope of FIG. 9 and the clinician defined area of interest maintaining its location on the patient's anatomy as the camera view changes.

With reference to FIG. 21, the software application of the synthesizer 300 enables the clinician to annotate or otherwise telestrate on the display screen 120 to selectively identify an area of interest on the real-time view of the patient's "P" lungs "L." The location at which the clinician placed the annotation "AN" on the real-time view of the patient's "P" lungs "L" is correlated to a location on the CLM by the software application. In this manner, the selected location is locked within the CLM (e.g., the position within the CLM is identified and stored) such that as the orientation of the surgeons view changes, the location of the annotation "AN" remains in the correct location on the CLM. In embodiments, the annotation "AN" may be highlighted on the CLM such that the clinician is able to observe the location of the annotation "AN" relative to the surgical instrument 400 (FIG. 22). The software application further assists the clinician in navigating the surgical instrument 400 to the location of the annotation "AN" using a navigation system.

The software application may use any suitable means for tracking the distal tip of the surgical instrument 400 within the patient's "P" body cavity. In this manner, a distal portion of the surgical instrument 400 includes a sensor 402 (FIG. 18) disposed thereon capable of being tracked using a tracking module 404, reference sensors 406, and a transmitter mat 408 (FIG. 1). In embodiments, the position of the distal tip of the surgical instrument 400 may be tracked using a robotic surgical system (not shown) or the like. With reference again to FIG. 1, a tracking system 410 including a navigation system capable of guiding the surgical instrument 400 within the thoracic cavity and the patient's "P" lungs "L" to the AOI is illustrated. The patient "P" is shown lying on the operating table 140 with the surgical instrument 400 advanced within the thoracic cavity using any suitable surgical device capable of permitting a surgical instrument to pass through a patient's "P" chest, such as an access port, trocar, or the like (not shown).

In one non-limiting embodiment, the navigation system may be a six degree-of-freedom electromagnetic tracking system, e.g., similar to those disclosed in U.S. Patent Application Publication No. 2016/0000302 to Brown et al., titled "System and Method for Navigating within the Lung," filed Jun. 29, 2015 and published PCT Application Nos. WO 00/10456 and WO 01/67035, the entire content of each of which is incorporated by reference herein, or another suitable positioning measuring system, is utilized for performing registration and navigation, although other configurations are also contemplated. The tracking system 410 includes the tracking module 404, the plurality of reference sensors 406, and the transmitter mat 408. The tracking system 410 is configured for use with the surgical instrument 410 and/or the thoracoscope 510 having sensor 402 and 510a (FIGS. 19 and 9, respectively), disposed at a distal portion thereof that enables monitoring of the position and orientation of the distal portion of the surgical instrument 400 and/or thoracoscope 510, in six degrees of freedom, relative to the reference coordinate system. For a detailed description of the construct of exemplary navigation systems, reference can be made to U.S. Patent Application Publication No. 2015/0265257 to Costello et al., titled "Systems, and Methods for Navigating a Biopsy Tool to a Target Location and Obtaining a Tissue Sample Using the Same," filed Dec. 9, 2014, the entire content of which is incorporated by reference herein.

The transmitter mat 408 is positioned beneath the patient "P" (FIG. 1) and is a transmitter of electromagnetic radiation and includes a stack of three substantially planar rectangular loop antennas (not shown) configured to be connected to drive circuitry (not shown). For a detailed description of the construction of exemplary transmitter mats, which may also be referred to as location boards, reference may be made to U.S. Pat. No. 9,575,140 to Zur, tiled "Magnetic Interference Detection System and Method," filed Apr. 2, 2009, the entire content of which is incorporated by reference herein.

The transmitter mat 408 and the plurality of reference sensors 406 are interconnected within the tracking module 404, which derives the location of each sensor 406 in six degrees of freedom. One or more of the reference sensors 406 are attached to the chest of the patient "P." The six degrees of freedom coordinates of the reference sensors 406 are sent to the computer 110 (which includes the appropriate software) where they are used to calculate a patient coordinate frame for reference. Registration is generally performed by identifying locations in both the 3D model and the patient's "P" thoracic cavity and/or lungs "L" and measuring the coordinates in both systems. These coordinates are then correlated and the two coordinate systems are aligned.

Figure 23:
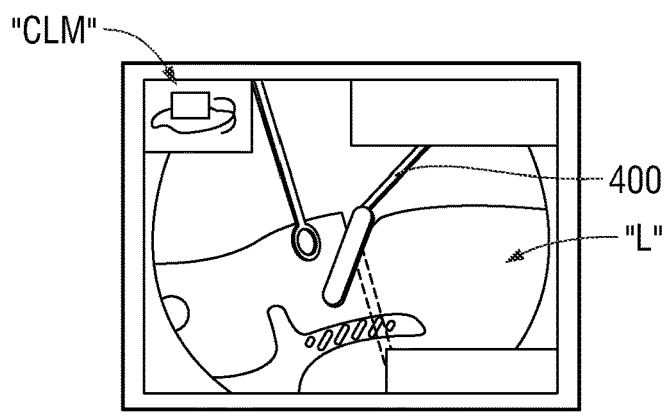
FIG. 23 is an illustration of the user interface of the system of FIG. 1, showing a camera view from the thoracoscope of FIG. 9 and instrument tracking information shown in a text box notifying the clinician of the distance the surgical instrument is from critical structures or the area of interest.

In use, the surgical instrument 400 is advanced within the thoracic cavity of the patient "P." Automatic registration is performed by moving the surgical instrument 400 through the thoracic cavity. More specifically, data pertaining to locations of the sensor 402 while the surgical instrument 400 is moving through the thoracic cavity is recorded using the tracking module 404, the reference sensors 406, and the transmitter mat 408. A shape resulting from this location data is compared to an interior geometry of the thoracic cavity and/or lungs "L" of the CLM, and a location correlation between the shape and the CLM based on the comparison is determined, e.g., utilizing the software on the computer 110. It is contemplated that the location of the distal portion of the surgical instrument 400 may be displayed on the CLM such that the clinician may identify the position of the surgical instrument 400 within the thoracic cavity and/or lungs "L" of the patient "P." Further, the software application of the synthesizer 300 provides prompts or warnings to the clinician via the user interface 112 if the surgical instrument 400 is guided too close to critical structures within the patient's "P" body cavity or lungs "L." In a similar fashion, the software application provides prompts or warnings to the clinician via the user interface 112 if the clinician attempts to treat (e.g., divide, ligate, or the like) the wrong structure (or a structure not identified during pre-operative planning). As the surgical instrument 400 is navigated within the body cavity or the patient's "P" lungs "L," the software application displays a distance of the distal tip of the surgical instrument 400 from critical structures such as nodules or vessels (FIG. 23). To accommodate this functionality, the software application may require the clinician to identify critical structures of interest in the CLM. During the surgical procedure, the software application monitors the position of the surgical instrument's 400 distal tip relative to these identified critical structures. Although generally described as being monitored using the electromagnetic tracking system 410, it is contemplated that the distance of the distal tip of the surgical instrument 400 relative to identified critical structures may be monitored using, e.g., optical estimation (via the optical camera 516, a 3D camera, etc.), the structured light scanner 514, etc. As can be appreciated, the previously described prompts, warnings, positional information, etc. may be utilized to help guide robotic surgical systems or the like, and in particular, as robotic surgical systems gain increasing autonomy.

The electromagnetic waves generated by the transmitter mat 408 are received by the various sensor elements configured for use with the surgical instrument 400, and are converted into electrical signals that are sensed via the reference sensors 406. The tracking system 410 further includes reception circuitry (not shown) that has appropriate amplifiers and A/D converters that are utilized to receive the electrical signals from the reference sensors 406 and process these signals to determine and record the location data of the sensor 402 disposed on the surgical instrument 400. The computer 110 may be configured to receive the location data from the tracking system 410 and display the current location of the sensor 402 on the CLM and relative to the selected pathway generated during the planning phase, e.g., on the display screen 120, the monitoring equipment 130, or other suitable display. Thus, navigation of the surgical instrument 400 to the AOI and/or manipulation of the surgical instrument 400 relative to the AOI, as detailed above, can be readily achieved.

Once the surgical instrument 400 has been successfully navigated to the AOI, the clinician may remove or otherwise treat (e.g., ablate, resect, biopsy, ligate, etc.) the AOI using the surgical instrument 400. For a detailed description of exemplary planning and navigation of a surgical tool, reference may be made to U.S. Patent Application Publication No. 2016/0000302 to Brown et al., previously incorporated by reference herein.

As can be appreciated, the electromagnetic navigation system 410 may be utilized to navigate the thoracoscope 510 through the thoracic cavity and within the patient's "P" lungs "L" to the AOI. To facilitate such navigation, the display screen 120, the monitoring equipment 130, and/or any other suitable display may be configured to display the CLM including the selected pathway from the current location of the sensor 510a disposed on a distal portion of the thoracoscope 510 to the AOI. Navigation of the thoracoscope 510 to the AOI using the tracking system 410 is similar to that detailed above and thus, is not detailed hereinbelow for purposes of brevity.

In step S124, a database may be built over time using the data obtained during each medical procedure. In particular, the software application of the synthesizer 300 stores post-procedural patient information in the HIS 200 and correlates such information to the particular patient on which the particular procedure was performed. In this manner, the database indexes each patient according to a particular procedure, or in embodiments, any suitable value (e.g., age, sex, race, outcome, etc.), such that clinicians may review data obtained from similar patients to better predict the outcome of the procedure as well as the effects of the procedure being performed. As can be appreciated, once the database is populated with a number of procedures and/or patients, a clinician will be able to predict or otherwise determine whether the planned procedure would produce the desired clinical effects. For example, a patient suffering from emphysema affecting a portion of the lungs located in the upper portion of the right lobe may be correlated to a similar patient having emphysema affecting a portion of the lungs located in the upper portion of the right lobe whose data has been entered into the database. In this manner, the clinician is able to predict whether performing a particular procedure or treating a specific portion of the patient's lungs would produce the desired clinical effects. Indeed, by predicting whether a patient would benefit from a particular procedure or treatment, the clinician is able to reduce the number of procedures required to treat the patient (e.g., eliminating or vastly reducing a trial and error approach), thereby reducing pain, recovery time, and expense. Further, this predictive model provides a basis to determine whether a patient's outcome meets the prediction or falls short and if it falls short the clinician may be able to identify one or more aggravating factors not previously contemplated and perform further procedures. As can be appreciated, the data obtained during each procedure may be available to clinicians who may be performing a similar procedure or treating a similar patient in the future.

It is contemplated that the database may be utilized to store data relating to the type of instruments used during the procedure, the number of surgical fasteners used (e.g., clips, staples, sutures, etc.), positional information relating to each surgical instrument utilized, etc. Clinicians may utilize this information to better predict the number of surgical staple cartridges (or other fasteners) required to complete the surgical procedure, reduce surgical waste, and provide a means by which clinicians may educate themselves or one another on how to improve tool selection for a given surgical procedure.

In embodiments, the software application of the synthesizer 300 enables tracking of patient outcomes and develops trends as compared to other patients and/or other institutions (e.g., hospitals or clinics using different or similar systems from that described in detail herein). Further, the software application facilitates the collection of a comparison between the actual and predicted surgery duration, the instruments that were used and how much they were used, the resources consumed, and/or turnover time. Using this information, clinicians and management personnel are able to track resource utilization, the cost of each procedure being performed, and provide metrics through which clinicians and management personnel are able to track or develop improvements to both the surgeon and the organization (e.g., the hospital or hospital network).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A system for performing a surgical procedure, comprising:
 a thoracoscope; and
 a computing device operably coupled to the thoracoscope, the computing device including a processor and a memory storing thereon instructions, which when executed, cause the processor to:
  develop a model of a patient's anatomical structure;
  acquire live images from the thoracoscope of a patient's anatomy during the surgical procedure and process the acquired live images of the patient's anatomy;
  display the acquired live images of the patient's anatomy on a user interface associated with the computing device;
  superimpose critical structures within the patient over the displayed acquired live images of the patient's anatomy;
  determine a location of the thoracoscope within a body cavity of the patient where the acquired live images of the patient's anatomy were taken;
  display an overall view of the model of the patient's anatomical structure on the user interface, the displayed model including an indication of the determined location where the acquired live images of the patient's anatomy were taken, wherein the model is displayed on the user interface separate from the acquired live images of the patient's anatomy;
  update the displayed model of the patient's anatomical structure in real-time based on the acquired live images of the patient's anatomy; and update an orientation of the updated displayed overall view of the model of the patient's anatomical structure in real-time based on the acquired live images of the patient's anatomy.

2. The system according to claim 1, further comprising the memory storing thereon further instructions, which when executed, cause the processor to display a distance between a surgical instrument and the critical structures within the patient's body cavity on the user interface.

3. The system according to claim 1, further comprising the memory storing thereon further instructions, which when executed, cause the processor to display a CT image associated with the location where the acquired live images of the patient's anatomy were taken.

4. The system according to claim 1, further comprising the memory storing thereon further instructions, which when executed, cause the processor to display a timer associated with a duration of the surgical procedure.

5. The system according to claim 1, further comprising the memory storing thereon further instructions, which when executed, cause the processor to enable receipt of a selection of data to display relating to the surgical procedure on the user interface.

6. The system according to claim 1, wherein the model of the patient's anatomical structure is a model of the patient's lungs.

7. The system according to claim 6, further comprising the memory storing thereon further instructions, which when executed, cause the processor to identify a location of lymph nodes within the patient's lung and generate a lymph node map based on the identified locations of the lymph nodes.

8. The system according to claim 7, further comprising the memory storing thereon further instructions, which when executed, cause the processor to identify enlarged lymph nodes using patient data.

9. The system according to claim 8, further comprising the memory storing thereon further instructions, which when executed, cause the processor to display a status of each lymph node on the user interface, the status relating to a position of each lymph node, and which lymph nodes have been removed during the surgical procedure.

10. The system according to claim 1, wherein the model of the patient's anatomical structure is an anatomical structure selected from the group consisting of the liver, the spleen, the kidney, and the adrenal gland.

11. A system for performing a surgical procedure, comprising:
a thoracoscope; and
a computing device operably coupled to the thoracoscope, the computing device including a processor and a memory storing thereon instructions, which when executed, cause the processor to:
develop a collapsed model of a patient's anatomical structure;
acquire live images from the thoracoscope of a patient's anatomy during the surgical procedure and display the live images of the patient's anatomy on a user interface associated with the computer;
superimpose critical structures within the patient over the displayed live images of the patient's anatomy;
determine a location of the thoracoscope within a body cavity of the patient where the live images of the patient's anatomy were taken;
display an overall view of the collapsed model of the patient's anatomical structure on the user interface, the displayed overall view of the model including an indication of the determined location where the live images of the patient were taken, wherein the overall view of the collapsed model is displayed on the user interface separate from the live images of the patient's anatomy;
update the displayed model of the patient's anatomical structure in real-time based on the acquired live images; and
update an orientation of the updated displayed overall view of the model in real-time based on the acquired live images.

12. The system according to claim 11, further comprising the memory storing thereon further instructions, which when executed, cause the processor to display a distance between a surgical instrument and critical structures within the patient's body cavity on the user interface.

13. The system according to claim 11, further comprising the memory storing thereon further instructions, which when executed, cause the processor to display vitals of the patient on the user interface.

14. The system according to claim 11, further comprising the memory storing thereon further instructions, which when executed, cause the processor to display a CT image associated with the location where the acquired live images of the patient's anatomy were taken.

15. The system according to claim 11, wherein the collapsed model of the patient's anatomical structure is a collapsed model of the patient's lungs.

16. A system for performing a surgical procedure, comprising:
a surgical tool;
a display; and
a computing device operably coupled to the surgical tool and the display, the computing device including a processor and a memory storing thereon instructions, which when executed, cause the processor to:
develop a model of a patient's anatomical structure;
acquire live images of a patient's anatomy during the surgical procedure and process the acquired live images of the patient's anatomy, wherein the live images are acquired by the surgical tool from within a body cavity of the patient;
present, on the display, the acquired live images of the patient's anatomy on a user interface associated with the computing device;
superimpose critical structures within the patient over the presented acquired live images of the patient's anatomy;
determine a location of the surgical tool within a body cavity of the patient where the acquired live images of the patient's anatomy were taken;
display an overall view of the model of the patient's anatomical structure on the user interface, the displayed model including an indication of the determined location where the acquired live images of the patient's anatomy were taken, wherein the model is displayed on the user interface separate from the acquired live images of the patient's anatomy;
update the displayed model of the patient's anatomical structure in real-time based on the acquired live images of the patient's anatomy; and
update an orientation of the updated displayed overall view of the model of the patient's anatomical structure in real-time based on the acquired live images of the patient's anatomy.

17. The system according to claim 16, further comprising a surgical instrument, wherein the memory stores thereon further instructions, which when executed, cause the processor to display a distance between the surgical instrument and critical structures within the patient's body cavity on the user interface.

18. The system according to claim 16, wherein the model of the patient's anatomical structure is a collapsed model of the patient's lungs.

19. The system according to claim 18, further comprising the memory storing thereon further instructions, which when executed, cause the processor to identify a location of lymph nodes within the patient's lungs and generate a lymph node map based on the identified locations of the lymph nodes.

20. The system according to claim 19, further comprising the memory storing thereon further instructions, which when executed, cause the processor to identify enlarged lymph nodes using patient data.

* * * * *